(12) United States Patent
Dickey et al.

(10) Patent No.: US 11,826,422 B2
(45) Date of Patent: Nov. 28, 2023

(54) METHODS AND COMPOSITIONS FOR ADAPTIVE IMMUNE MODULATION

(71) Applicants: THE BOARD OF REGENTS OF THE UNIVERSITY OF TEXAS SYSTEM, Austin, TX (US); PULMOTECT, INC., Houston, TX (US); THE TEXAS A&M UNIVERSITY SYSTEM, College Station, TX (US)

(72) Inventors: Burton F. Dickey, Houston, TX (US); Michael J. Tuvim, Houston, TX (US); Scott E. Evans, Bellaire, TX (US); Magnus Hook, College Station, TX (US); David P. Huston, College Station, TX (US); Margarita Martinez-Moczygemba, College Station, TX (US); Brenton Scott, Houston, TX (US)

(73) Assignee: Board of Regents, the University of Texas System, Austin, TX (US)

( * ) Notice: Subject to any disclaimer, the term of this patent is extended or adjusted under 35 U.S.C. 154(b) by 792 days.

(21) Appl. No.: 16/348,829

(22) PCT Filed: Nov. 9, 2017

(86) PCT No.: PCT/IB2017/057025
§ 371 (c)(1),
(2) Date: May 9, 2019

(87) PCT Pub. No.: WO2018/087699
PCT Pub. Date: May 17, 2018

(65) Prior Publication Data
US 2019/0269773 A1    Sep. 5, 2019

Related U.S. Application Data

(63) Continuation of application No. 62/419,739, filed on Nov. 9, 2016.

(51) Int. Cl.
| | |
|---|---|
| A61K 39/39 | (2006.01) |
| A61K 9/00 | (2006.01) |
| A61K 31/7125 | (2006.01) |
| A61K 39/35 | (2006.01) |
| A61P 37/08 | (2006.01) |
| A61K 31/58 | (2006.01) |
| A61K 38/16 | (2006.01) |
| C12N 15/117 | (2010.01) |
| H04B 1/04 | (2006.01) |
| H04B 1/16 | (2006.01) |
| H04B 1/715 | (2011.01) |
| H04B 1/7156 | (2011.01) |
| H04B 1/40 | (2015.01) |
| H04B 1/713 | (2011.01) |
| A61K 39/00 | (2006.01) |

(52) U.S. Cl.
CPC .............. *A61K 39/35* (2013.01); *A61K 31/58* (2013.01); *A61K 38/164* (2013.01); *A61P 37/08* (2018.01); *C12N 15/117* (2013.01); *H04B 1/04* (2013.01); *H04B 1/16* (2013.01); *H04B 1/40* (2013.01); *H04B 1/713* (2013.01); *H04B 1/715* (2013.01); *H04B 1/7156* (2013.01); *A61K 2039/55561* (2013.01); *C12N 2310/315* (2013.01)

(58) Field of Classification Search
None
See application file for complete search history.

(56) References Cited

U.S. PATENT DOCUMENTS

| | | |
|---|---|---|
| 4,668,218 A | 5/1987 | Virtanen |
| 4,689,338 A | 8/1987 | Gerster |
| 4,929,624 A | 5/1990 | Gerster et al. |
| 5,238,944 A | 8/1993 | Wick et al. |

(Continued)

FOREIGN PATENT DOCUMENTS

| | | |
|---|---|---|
| EP | 0237507 | 9/1987 |
| JP | 2012-522001 | 9/2012 |

(Continued)

OTHER PUBLICATIONS

Yamazaki et al. TLR2-Dependent Induction of IL-10 and Foxp3+ CD25+CD4+ Regulatory T Cells Prevents Effective Anti-Tumor Immunity Induced by Pam2 Lipopeptides In Vivo(PLoS, 2011, 4:1-10). (Year: 2011).*

(Continued)

*Primary Examiner* — Arthur S Leonard
(74) *Attorney, Agent, or Firm* — Norton Rose Fulbright US LLP

(57) ABSTRACT

Embodiments are directed to methods and compositions for modulating an immune response. In certain aspects the immune response is a type I hypersensitivity response. In particular aspects the subject has allergic asthma or allergic rhinitis. Using a conventional experimental asthma mouse model (BALB/c), the inventors demonstrate that aerosol administration of TLR agonists, in particular a combination of TLR2/6 and TLR9 agonist (e.g., TLR9 oligonucleotide agonist/PAM2CSK4) along with an antigen (e.g., ovalbumin (OVA)) suppresses the immune response as exemplified by the production of antigen-specific IgE and decreases the number of airway eosinophils in bronchoalveolar lavage fluid (BAL) in response to intraperitoneal (IP) immunization with an antigen mixed with alum.

9 Claims, 10 Drawing Sheets
Specification includes a Sequence Listing.

(56) References Cited

U.S. PATENT DOCUMENTS

| | | | |
|---|---|---|---|
| 5,266,575 | A | 11/1993 | Gerster et al. |
| 5,268,376 | A | 12/1993 | Gester |
| 5,346,905 | A | 9/1994 | Gerster |
| 5,352,784 | A | 10/1994 | Nikolaides et al. |
| 5,389,640 | A | 2/1995 | Gerster et al. |
| 5,395,937 | A | 3/1995 | Nikolaides et al. |
| 5,458,135 | A | 10/1995 | Patton et al. |
| 5,482,936 | A | 1/1996 | Lindstrom |
| 5,494,916 | A | 2/1996 | Lindstrom et al. |
| 5,525,612 | A | 6/1996 | Gerster |
| 6,039,969 | A | 3/2000 | Tomai et al. |
| 6,110,929 | A | 8/2000 | Gerster et al. |
| 6,331,539 | B1 | 12/2001 | Crooks et al. |
| 6,488,953 | B2 | 12/2002 | Halliday et al. |
| 6,737,045 | B2 | 5/2004 | Patton et al. |
| 6,794,357 | B1 | 9/2004 | Backstrom et al. |
| 6,797,258 | B2 | 9/2004 | Platz et al. |
| 10,286,065 | B2 * | 5/2019 | Dickey ............. A61K 31/7056 |
| 2003/0225016 | A1 | 12/2003 | Fearon et al. |
| 2004/0067902 | A9 | 4/2004 | Bratzler et al. |
| 2004/0162309 | A1 | 8/2004 | Gorden et al. |
| 2004/0171086 | A1 | 9/2004 | Fink et al. |
| 2007/0037767 | A1 | 2/2007 | Bratzler et al. |
| 2009/0081157 | A1 * | 3/2009 | Kornbluth ............. A61K 39/21 424/85.2 |
| 2009/0176696 | A1 * | 7/2009 | Mills ....................... A61P 37/08 514/1.1 |
| 2012/0237546 | A1 | 9/2012 | Singh et al. |
| 2015/0004688 | A1 | 1/2015 | Kinzler et al. |
| 2015/0196636 | A1 * | 7/2015 | Mudde ........... A61K 39/001141 424/173.1 |
| 2016/0082103 | A1 | 3/2016 | Dickey et al. |

FOREIGN PATENT DOCUMENTS

| | | |
|---|---|---|
| JP | 2015-527313 | 9/2015 |
| WO | WO 94/06498 | 3/1994 |
| WO | WO 94/08552 | 4/1994 |
| WO | WO 94/16970 | 8/1994 |
| WO | WO 97/25086 | 7/1997 |
| WO | WO 98/16427 | 4/1998 |
| WO | WO 98/35888 | 8/1998 |
| WO | WO 98/55495 | 12/1998 |
| WO | WO 00/76518 | 12/2000 |
| WO | WO 02/46189 | 6/2002 |
| WO | WO 02/46192 | 6/2002 |
| WO | WO 02/46193 | 6/2002 |
| WO | WO 2008/139262 | 11/2008 |
| WO | WO 2009/088401 | 7/2009 |
| WO | WO 2010/111485 | 9/2010 |
| WO | 2357184 | 8/2011 |
| WO | WO 2012/049312 | 4/2012 |
| WO | WO 2014/082254 | 6/2014 |
| WO | WO 2015/181298 | 12/2015 |
| WO | WO 2016/161372 | 10/2016 |

OTHER PUBLICATIONS

Shirota et al., Regulation of Murine Airway Eosinophilia and Th2 Cells by Antigen-Conjugated CpG Oligodeoxynucleotides as a Novel Antigen-Specific Immunomodulator (J Imm, 2000, 164:5575-5582) (Year: 2000).*

Kim et al. "CpG Oligodeoxynucleotide Inhibits Cockroach-Induced Asthma via Induction of IFN-γ+ Th1 Cells or Foxp3+ Regulatory T Cells in the Lung" *Allergy, Asthma & Immunology Research* vol. 8, No. 3, pp. 264-275, May 2016.

Krishnaswamy et al. "Toll-Like Receptor-2 Agonist-Allergen Coupling Efficiently Redirects Th2 Cell Responses and Inhibits Allergic Airway Eosinophilia" *Am J Respor Cell Mol Biol* vol. 47. Iss 6, pp. 852-863, Dec. 2012.

Kulis & BUrks "Oral immunotherapy for food allergy: Clinical and preclinical studies" *Advanced Drug Delivery Reviews* 65 (2013) 774-781.

Barnes, Peter,, "Immunology of asthma and chronic obstructive pulmonary disease" *Nature Reviews Immunology*, 2008, 8:183-192.

Clement et al., "Stimulation of Lung Innate Immunity Protects against Lethal Pneumococcal Pneumonia in Mice" *Am J. Respir Crit Care Med.*, 2008, 177:1322-1330.

Duggan et al., "Synergistic Interactions of TLR2/6 and TLR 9 Induce a High Level of Resistance to Lung Infection in Mice" *J. Immunol.*, 2011, 186(10):5916-5926.

Evans et al., "Inducible innate resistance of lung epithelium to infection" *Annu Rev. Physiol.*, 2010, 72:413-435.

Evans et al., "Inhaled innate immune ligands to prevent pneumonia" *Am. J. Respir. Cell Mol. Biol.*, 2010, 42:40-50.

Evans et al., "Inhaled innate immune ligands to prevent pneumonia" *Br. J. Pharmacol.*, 2011, 163:195-206.

Fanta, Christopher, "Asthma" *N. Engl. J. Med.*, 2009, 360:1002-1014.

Ferrandon et al., "The *Drosophila* systemic immune response: sensing and signaling during bacterial and fungal infections" *Nat. Rev. Immunol.*, 2007, 7:862-874.

International Search Report and Written Opinion issued in Corresponding International Patent Application No. PCT/IB2017/057025, dated Apr. 27, 2018.

James et al., "Long-term tolerance after allergen immunotherapy is accompanied by selective persistence of blocking antibodies" *J. Allergy Clin Immunol.*, 2011, 127:509-516.

Karsten et al., "Galactosylated IgG1 linke FcγRIIb and Dectin-1 to block complement-mediated inflammation" *Nat. Med.*, 2012, 18:1401-1406.

Krug et al., "Identification of CpG oligonucleotide sequences with high induction of IFNα/β in plasmacytoid dendritic cells." *Eur. J. Immunol.*, 2001, 31(7):2154-5163.

Marshall et al., "Superior activity of the type C class of ISS in vitro and in vivo across multiple species" *DNA Cell Biol.*, 2005, 24(2):63-72.

Mizgerd, J.P., "Acute lower respiratory tract infection" *N. Engl. J. Med.*, 2008, 358:716-727.

Tuvim et al., "Synergistic TLR2/6 and TLR9 Activation Protects Mice against Lethal Influenza Pneumonia" *PLoS One*, 2009, 4:e4176.

West et al., "Recognition and Signaling by Toll-Like Receptors" *Annu. Rev. Cell Dev. Biol.*, 2006, 22:409-437.

Extended European Search Report Issued by European Patent Application No. EP 17870060.5, dated May 20, 2020.

Decision to Grant issued by the Japan Patent Office in corresponding Japanese patent application No. 2019-525874 dated Aug. 22, 2022.

Johansen et al, "Toll-like receptor ligands as adjuvants in allergen-specific immunotherapy", *Clin Exp Allergy*, 35:1591-1598, 35.

* cited by examiner

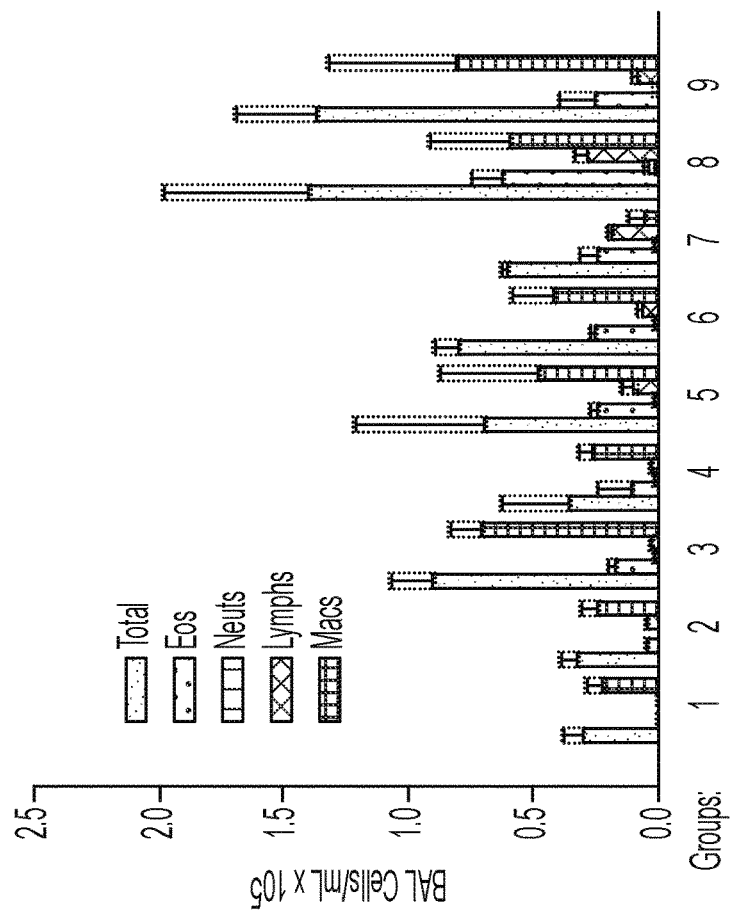
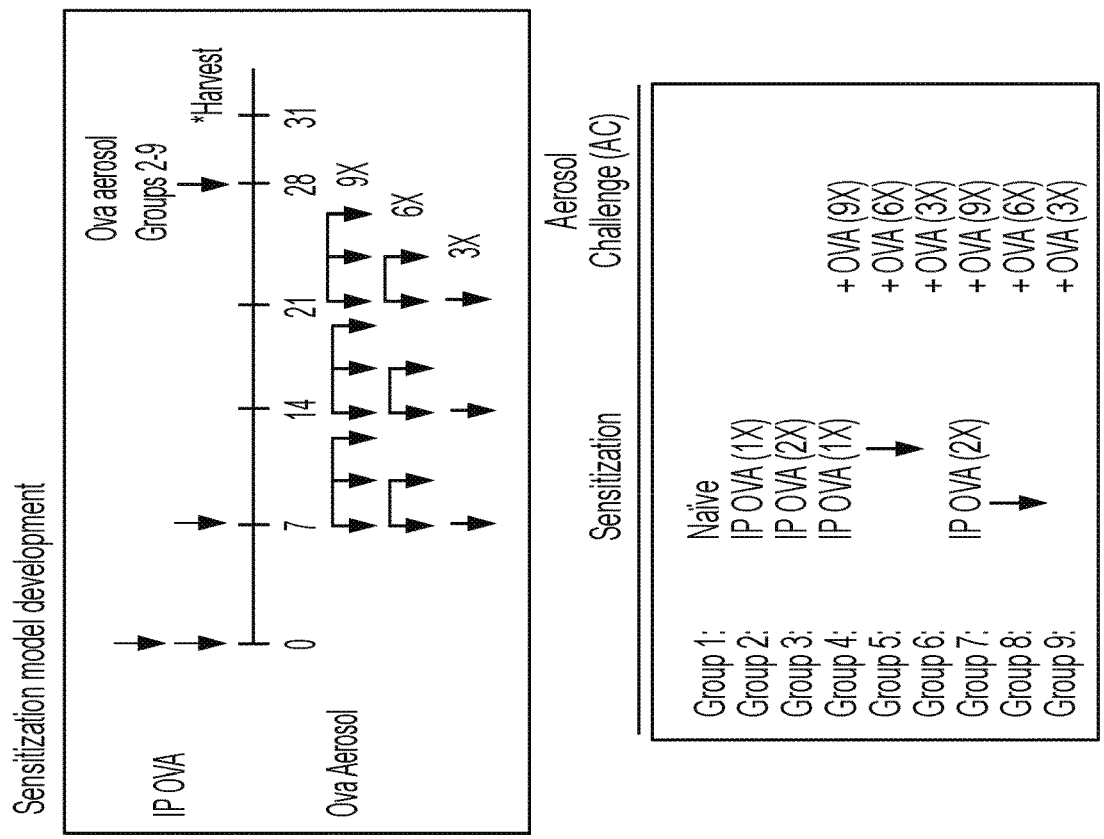
FIG. 3A
FIG. 3B

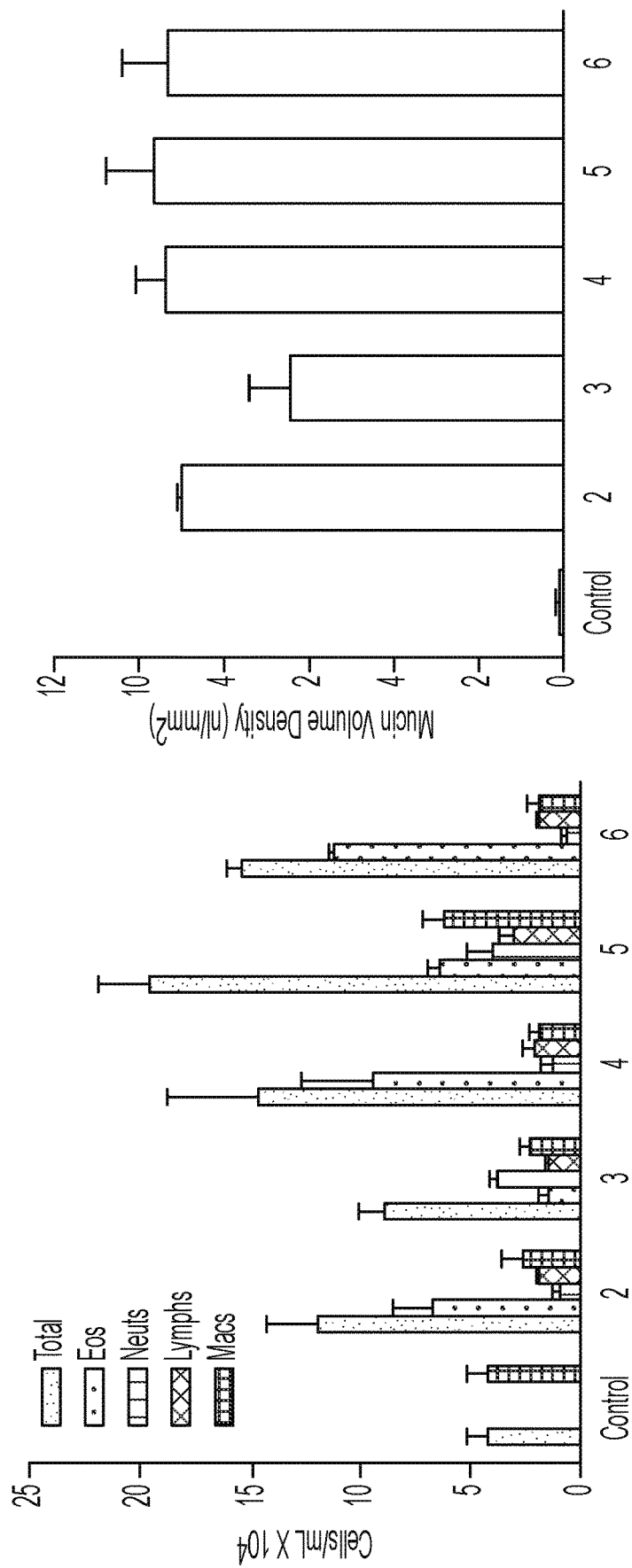

METHODS AND COMPOSITIONS FOR ADAPTIVE IMMUNE MODULATION

CROSS-REFERENCE TO RELATED APPLICATIONS

The present application is a national phase under 35 U.S.C. § 371 of International Application No. PCT/IB2017/057025, filed Nov. 9, 2017, which claims priority to U.S. Provisional Patent Application Ser. No. 62/419,739, filed Nov. 9, 2016, each of which are incorporated herein by reference in their entirety.

STATEMENT REGARDING FEDERALLY FUNDED RESEARCH

This invention was made with government support under R43 HL115903 awarded by the National Institutes of Health. The government has certain rights in the invention.

REFERENCE TO SEQUENCE LISTING

A sequence listing required by 37 CFR 1.821-1.825 is being submitted electronically with this application. The sequence listing is incorporated herein by reference.

PARTIES TO JOINT RESEARCH AGREEMENT

Certain embodiments described herein were made as a result of activities undertaken within the scope of a joint research agreement that was in effect at the time the present invention was made. The parties to said joint research agreement are Board of Regents of the University of Texas System and The Texas A&M University System.

BACKGROUND

Asthma is a complex inflammatory disease of the lungs characterized by eosinophilic inflammation, elevated serum IgE levels, mucus production, and reversible airflow obstruction. The currently available therapeutics for treating allergic asthma provide immediate symptomatic relief and some even reduce airway inflammation; however, they remain inadequate. Thus, additional strategies for treating allergic diseases are needed.

IgE plays an essential role in type I hypersensitivity, which manifests various allergic diseases, such as allergic asthma, allergic rhinitis, food allergy, and some types of chronic urticaria and atopic dermatitis. IgE also plays a pivotal role in allergic conditions, such as anaphylactic reactions to certain drugs, bee stings, and antigen preparations used in specific desensitization immunotherapy.

SUMMARY

Embodiments are directed to methods and compositions for modulating an immune response, as well as composition and methods for mitigating lower respiratory infections in patients with underlying inflammatory disease (e.g., COPD). In certain aspects the immune response is an allergic immune response. In certain aspects the immune response is a type I hypersensitivity response. In further aspects the immune response is an IgE mediated immune response. In particular aspects the subject has allergic asthma or allergic rhinitis. Using a conventional experimental asthma mouse model (BALB/c), the inventors demonstrate that aerosol administration of TLR agonists, in particular a combination of TLR2/6 and TLR9 agonist (e.g., TLR9 oligonucleotide agonist (O)/PAM2CSK4 (S-[2,3-bis(palmitoyloxy)-(2RS)-propyl]-[R]-cysteinyl-[S]-seryl-[S]-lysyl-[S]-lysyl-[S]-lysyl-[S]-lysinex3 CF3COOH) (P) along with an antigen (e.g., ovalbumin (OVA)) suppresses the immune response as exemplified by the production of antigen-specific IgE and decreases the number of airway eosinophils in bronchoalveolar lavage fluid (BAL) in response to intraperitoneal (IP) immunization with an antigen mixed with alum. In contrast, serum levels of mouse IgG2a, a marker of Th1 immunity, increased in the O/P-OVA challenge model. These findings indicate that administration of a combination of aerosolized O/P and antigen has the capacity to deviate the immune response away from Type 2 allergic inflammation resulting from exposure to the antigen.

In some embodiments, the methods and compositions described herein can be used to treat hypersensitivity. As used herein, "hypersensitivity" refers to an undesirable immune system response. Hypersensitivity is divided into four categories. Type I hypersensitivity includes allergies (e.g., Atopy, Anaphylaxis, or Asthma). Type II hypersensitivity is cytotoxic/antibody mediated (e.g., Autoimmune hemolytic anemia, Thrombocytopenia, Erythroblastosis fetalis, or Goodpasture's syndrome). Type III is immune complex diseases (e.g., Serum sickness, Arthus reaction, or SLE). Type IV is delayed-type hypersensitivity (DTH), Cell-mediated immune memory response, and antibody-independent (e.g., Contact dermatitis, Tuberculin skin test, or Chronic transplant rejection). In certain embodiments, the subject has been diagnosed with the disease or condition or has been previously treated for the disease or condition. It is specifically contemplated that the subject is a human subject in certain embodiments. In other embodiments, the subject is a mammal that can develop or have the indicated disease or condition or experience the physiologic effects described herein.

As used herein, "allergy" means a disorder characterized by excessive activation of mast cells and basophils by IgE. In certain instances, the excessive activation of mast cells and basophils by IgE results (either partially or fully) in an inflammatory response. In certain instances, the inflammatory response is local. In certain instances, the inflammatory response results in the narrowing of airways (i.e., bronchoconstriction). In particular instances, the inflammatory response results in inflammation of the nose (i.e., rhinitis). In certain instances, the inflammatory response is systemic (i.e., anaphylaxis).

Additional aspects are directed to methods for attenuating a type 2 allergic response or antigen specific IgE levels in a subject, comprising administering an effective amount of at least two TLR agonists to a subject susceptible to type I hypersensitivity, e.g., allergies and/or allergen induced asthma. In certain aspects the subject has been exposed to an allergen. It is contemplated that the response or antigen-specific IgE levels is reduced in some embodiments. In other aspects the composition is administered prophylactically. In a further aspect the composition is administered prophylactically to an asthmatic or type I hypersensitive subject. In a further aspect the TLR agonists are selected from the group consisting of TLR2/1, TLR2/6, TLR3, TLR4, TLR5, TLR9, and TLR7 agonist. In certain aspects the TLR agonist composition comprises a TLR9 agonist and a TLR2/6 agonist. The TLR2/6 agonist can be a diacylated lipopolypeptide, such as PAM2CSK4. The TLR9 agonists can be an TLR9 oligonucleotide agonist, including but not limited to type A CpG oligodeoxynucleotide, a type B CpG oligodeoxynucleotide, a type C CpG oligodeoxynucleotides or other oligodeoxynucleotides. In certain aspects the TLR9 oligonucleotide agonist is a type C oligodeoxynucleotide (ODN), such as ODN2395 (5'-tcgtcgttttcggcgcgcgccg-3' (22 mer) (SEQ ID NO:1)) or ODNM362 (5'-tcgtcgtcgttcgaacgacgttgat-3' (25 mer) (SEQ ID NO:2)) or ODN10101 (5'-tcgtcgttttcgcgcgcgccg-3' (SEQ ID NO:3)) or 9 mer (5'-cgcgaagcg-3' (SEQ ID NO:4)) or H-Tel 22 (5'-aggggttagggttagggttaggg-3' (SEQ ID NO:5)) or analog thereof. In particular aspects the TLR9 oligonucleotide has a phosphorothioate or phosphodiester backbone. Certain formulations or methods can include administration of 1, 2, 3, 4, or more TLR9 oligonucleotide agonist individually or in combination. The TLR agonist composition can include an anti-inflammatory agent and/or other pharmaceutically acceptable excipient. In certain aspects the anti-inflammatory agent is selected from betamethasone, triamcinolone, dexamethasone, prednisone, mometasone, flunisolide and budesonide, particularly budesonide. In certain aspects the pharmaceutical excipient is glycerol.

In certain aspects the TLR agonist composition comprises PAM2CSK4 and an TLR9 oligonucleotide agonist. In particular aspects the TLR 9 In certain aspects molar ratio of TLR2/6 agonist (e.g., PAM2CSK) to TLR9 agonist (e.g., ODN) is or is about 1:1, 2:1, 3:1, 4:1, 5:1, 6:1, 7:1, 8:1, 1:2, 1:3, 1:4, 1:5, 1:6, 1:7, or 1:8. In certain aspects the TLR agonist composition is administered in combination with an allergen. In certain aspects the allergen is administered or a subject is exposed to the allergen before; during; after; before and during; before and after; during and after; or before, during and after administration of the TLR agonist composition. The compositions can be administered 1, 2, 3, 4, 5, 6, 7, 8, 9, 10 or more times (or any range derivable therein). In certain aspects the compositions are administered every 4, 6, 8, 10, 12, or 24 hours, or every 1, 2, 3, 4, 5, 6, 7 days, weeks, or months, and any range derivable therein. In certain aspects the compositions are administered continually on a daily or weekly basis.

Certain embodiments are directed to suppressing type 2 (or Th2 mediated) allergic inflammation or type I hypersensitivity by administering a combination of TLR agonist. In certain aspects a target antigen or allergen is administered in combination with TLR agonist composition. In further embodiments, the subject has been diagnosed with or identified as having chronic asthma. In other embodiments, the subject has been diagnosed with and/or evaluated for type-2 allergies prior to being given the TLR agonists. In certain embodiments, the patient is already being treated for allergy or asthma. In some methods, the patient is also administered asthma medication, such as a corticosteroid, epinephrine, or short-term beta2-agonist. In other embodiments, additionally or alternatively, the patient is taking an antihistamine or other allergy treatment. In some embodiments, the patient is taking an immune-suppressant.

Type I hypersensitivity (or immediate hypersensitivity) is an allergic reaction provoked by reexposure to a specific type of antigen referred to as an allergen. Type I is not to be confused with Type II, Type III, or Type IV hypersensitivities. Exposure may be by ingestion, inhalation, injection, or direct contact.

In type 1 hypersensitivity, an antigen is presented to CD4+Th2 cells specific to the antigen that stimulates B-cell production of IgE antibodies also specific to the antigen. The difference between a normal infectious immune response and a type 1 hypersensitivity response is that in type 1 hypersensitivity the antibody is IgE instead of IgA, IgG, or IgM. During sensitization, the IgE antibodies bind to FCC receptors on the surface of tissue mast cells and blood basophils. Mast cells and basophils coated by IgE antibodies are "sensitized." Later exposure to the same allergen cross-links the bound IgE on sensitized cells, resulting in degranulation and the secretion of pharmacologically active mediators such as histamine, leukotriene (LTC4 and LTD4), and prostaglandin that act on the surrounding tissues. The principal effects of these products are vasodilation and smooth-muscle contraction.

As used herein, the term "antigen" is a molecule capable of being bound by an antibody or T-cell receptor. An antigen is additionally capable of inducing a humoral immune response and/or cellular immune response leading to the production of B- and/or T-lymphocytes. The structural aspect of an antigen, e.g., three-dimensional conformation or modification (e.g., phosphorylation), giving rise to a biological response is referred to herein as an "antigenic determinant" or "epitope." B-lymphocytes respond to foreign antigenic determinants via antibody production, whereas T-lymphocytes are the mediator of cellular immunity. Thus, antigenic determinants or epitopes are those parts of an antigen that are recognized by antibodies, or in the context of an MHC, by T-cell receptors. An antigenic determinant need not be a contiguous sequence or segment of protein and may include various sequences that are not immediately adjacent to one another. In certain embodiments, binding moieties other than antibodies and be engineered to specifically bind to an antigen, e.g., aptamers, avimers, and the like.

As used herein the term "allergen" is a substance(s) containing antigens that can cause an undesired (e.g., a Type 1 hypersensitive) immune response (i.e., an allergic response or reaction) in a subject. Allergens include, but are not limited to, plant allergens (e.g., pollen, ragweed allergen), insect allergens, insect sting allergens (e.g., bee sting allergens), animal allergens (e.g., pet allergens, such as animal dander or cat Fel d 1 antigen), latex allergens, mold allergens, fungal allergens, cosmetic allergens, drug allergens, food allergens, dust, insect venom, viruses, bacteria, etc. Food allergens include, but are not limited to milk allergens, egg allergens, nut allergens (e.g., peanut or tree nut allergens, etc.), fish allergens, shellfish allergens, soy allergens, legume allergens, seed allergens and wheat allergens. Insect sting allergens include allergens that are or are associated with bee stings, wasp stings, hornet stings, yellow jacket stings, etc. Insect allergens also include house dust mite allergens (e.g., Der P1 antigen) and cockroach allergens. Drug allergens include allergens that are or are associated with antibiotics, NSAIDs, anesthetics, etc. Pollen allergens include grass allergens, tree allergens, weed allergens, flower allergens, etc. Subjects that develop or are at risk of developing an undesired immune response to any of the allergens provided herein may be treated with any of the compositions and methods provided herein. Subjects that may be treated with any of the compositions and methods provided also include those who have or are at risk of having an allergy to any of the allergens provided. "Allergens associated with an allergy" are allergens that generate an undesired immune response that results in, or would be expected by a clinician to result in, alone or in combination with other allergens, an allergic response or reaction or a symptom of an allergic response or reaction in a subject. "Type(s) of allergens" means molecules that share the same, or substantially the same, antigenic characteristics in the context of an undesired immune response. In some embodiments, the allergens may be proteins, polypeptides, peptides, or lipoproteins.

Certain embodiments are directed to compositions and methods for treating (including prophylactic treatment) or ameliorating a respiratory infection, in particular a lower respiratory infection. In certain aspect the subject being treated has an underlying inflammatory disease. Certain aspects are directed to a formulation or a method of administering an effective amount of a TLR9 agonist and a TLR2/6 agonist to an individual that has or is at risk of developing or acquiring a microbial infection. In certain aspects the TLR2/6 agonist is a diacylated lipopeptide, such as PAM2CSK4. In a further aspect the TLR9 agonist is an TLR9 oligonucleotide agonist. The TLR9 agonists can be an TLR9 oligonucleotide agonist, including but not limited to type A CpG oligodeoxynucleotide, a type B CpG oligodeoxynucleotide, a type C CpG oligodeoxynucleotides or other oligodeoxynucleotides. In certain aspects the TLR9 oligonucleotide agonist is ODN2395 (5'-tcgtcgttttcggcgcgcgccg-3' (22 mer) (SEQ ID NO:1)) or ODNM362 (5'-tcgtcgtcgttcgaacgacgttgat-3' (25 mer) (SEQ ID NO:2)) or ODN10101 (5'-tcgtcgttttcgcgcgcgccg-3' (SEQ ID NO:3)) or 9 mer (5'-cgcgaagcg-3' (SEQ ID NO:4)) or H-Tel 22 (5'-agggttagggttagggttaggg-3' (SEQ ID NO:5)) or analog thereof. In particular aspects the TLR9 oligonucleotide has a phosphorothioate or phosphodiester backbone. Certain formulations or methods can include administration of 1, 2, 3, 4, or more TLR9 oligonucleotide agonist individually or in combination.

In other aspects the TLR9 agonist and the TLR2/6 agonist are administered in a nebulized formulation. The TLR9 agonist and/or the TLR2/6 agonist can be administered in an amount from about 0.1, 1, 5, 10, 50 μg or mg/kg to about 5, 10, 50, 100 μg or mg/kg of the individual's body weight, including all values and ranges there between.

Certain embodiments are directed to a pharmaceutically acceptable composition comprising a TLR9 agonist and a TLR2/6 agonist, an anti-inflammatory agent, and one or more pharmaceutical excipients, wherein said composition is sterile and essentially free of pathogenic microbes. In certain aspects the TLR2/6 agonist is a diacylated lipopeptide, such as PAM2CSK4. In a further aspect the TLR9 agonist is a TLR9 oligonucleotide agonist. An anti-inflammatory agent can be selected from betamethasone, triamcinolone, dexamethasone, prednisone, mometasone, flunisolide and budesonide, particularly budesonide. In certain aspects the pharmaceutical excipient is glycerol.

The term "isolated" can refer to a nucleic acid or polypeptide that is substantially free of cellular material, bacterial material, viral material, or culture medium (when produced by recombinant DNA techniques) of their source of origin, or chemical precursors or other chemicals (when chemically synthesized). Moreover, an isolated compound refers to one that can be administered to a subject as an isolated compound; in other words, the compound may not simply be considered "isolated" if it is adhered to a column or embedded in an agarose gel. Moreover, an "isolated nucleic acid fragment" or "isolated peptide" is a nucleic acid or protein fragment that is not naturally occurring as a fragment and/or is not typically in the functional state.

Moieties of the invention, such as polypeptides, peptides, antigens, allergens, or immunogens, may be conjugated or linked covalently or noncovalently to other moieties such as adjuvants, proteins, peptides, supports, fluorescence moieties, or labels. The term "conjugate" or "immunoconjugate" is broadly used to define the operative association of one moiety with another agent and is not intended to refer solely to any type of operative association, and is particularly not limited to chemical "conjugation."

The term "providing" is used according to its ordinary meaning "to supply or furnish for use." In some embodiments, the protein is provided directly by administering the protein, while in other embodiments, the protein is effectively provided by administering a nucleic acid that encodes the protein. In certain aspects the invention contemplates compositions comprising various combinations of nucleic acid, antigens, peptides, and/or epitopes. An allergen or antigen may be administered to the subject concurrently with one or more TLR agonists. In some embodiments, it is in the same composition as 1, 2, 3, or more TLR agonists. Moreover, it may be attached to one or more TLR agonists.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

(FIG. 1A) Allergic sensitization mouse model. Balb/c mice (n=10) were immunized twice, two weeks apart with OVA/alum by IP injection. On the day of the first immunization, mice in Group 3 were given aerosol challenges with OVA-O/P three times/week, (+OVA-O/P, 9×). On the day of the second immunization, aerosol challenges with either OVA/alum alone (Group 6), O/P alone (Group 5), OVA-O/P (6×, Group 4), or OVA given in combination with individual O/P components were administered three times/week for 2 weeks (6×, Group 7 and 8). Mice were harvested on day 21 for serologic and BAL analyses. (FIG. 1B) Serum from mice in 1A was analyzed by sandwich ELISAs to measure total IgE. A significant decrease in total IgE between mice treated with OVA alone (Group 6, 17.23±1.82) and mice treated with OVA-O/P (9×) was detected (Group 3, 3.69±0.53, P=0.0001). (FIG. 1C) Serum from same mice was used to measure OVA-specific IgE. Comparison of mice treated with OVA alone (C, Group 6, 4.36±0.82) with mice treated with OVA plus O/P (Group 4, 1.24±0.26, p=0.005) revealed a 70% reduction in OVA-specific IgE indicating a blunted allergic response. Lastly, comparison of Group 6 with group 3 revealed an even more significant difference (Group 6: 4.36±0.82 vs. Group 3: 0.35±0.7, P=0.0008).

FIGS. 3A-3B. Allergic sensitization optimization with OVA as measured by inflammatory cells in BAL. (FIG. 3A) Balb/c mice (n=10) were immunized either once (Group 2.4-6) or twice (Group 3, 7-9), one week apart with OVA/alum by IP injection. On day 7, aerosol challenges with OVA/alum alone were administered once/week (Group 6 and 9), two times/week (Group 5 and 8), or three times/week for 2 weeks (Group 4 and 7). Mice were harvested on day 31 for serologic and BAL analyses. (FIG. 3B) BAL from mice in 3A were analyzed for total and differential cell counts by Wright-Giemsa staining. Note how eosinophils (EOS) in Group 8 are elevated compared to all other groups.

FIGS. 5A-5C. Inflammatory cell and mucin analysis for determination of most efficacious window with aerosolized OVA-O/P. (FIG. 5A) BALB/c mice (n=10) were immunized and aerosol challenged with either OVA alone (Group 2), or with OVA-0/P at various intervals as illustrated in FIG. 5A. (FIG. 5B) BAL was collected from six groups of mice (n=5) and total and differential cell counts were determined as described in Materials and Methods. Mice in Group 3 appear to have the least amount of EOS (orange bar) in the BAL as compared to other four groups. (FIG. 5C) After BAL harvest, lungs were fixed with 10% formalin, embedded into paraffin and cut into 3 μm sections before staining with periodic acid Schiff (PAS) for mucin density analysis from six groups (n=5). Mice in Group 3 appear to have the lowest mucin density as compared to other groups, which is consistent with FIG. 5B.

DESCRIPTION

Figure 1A:
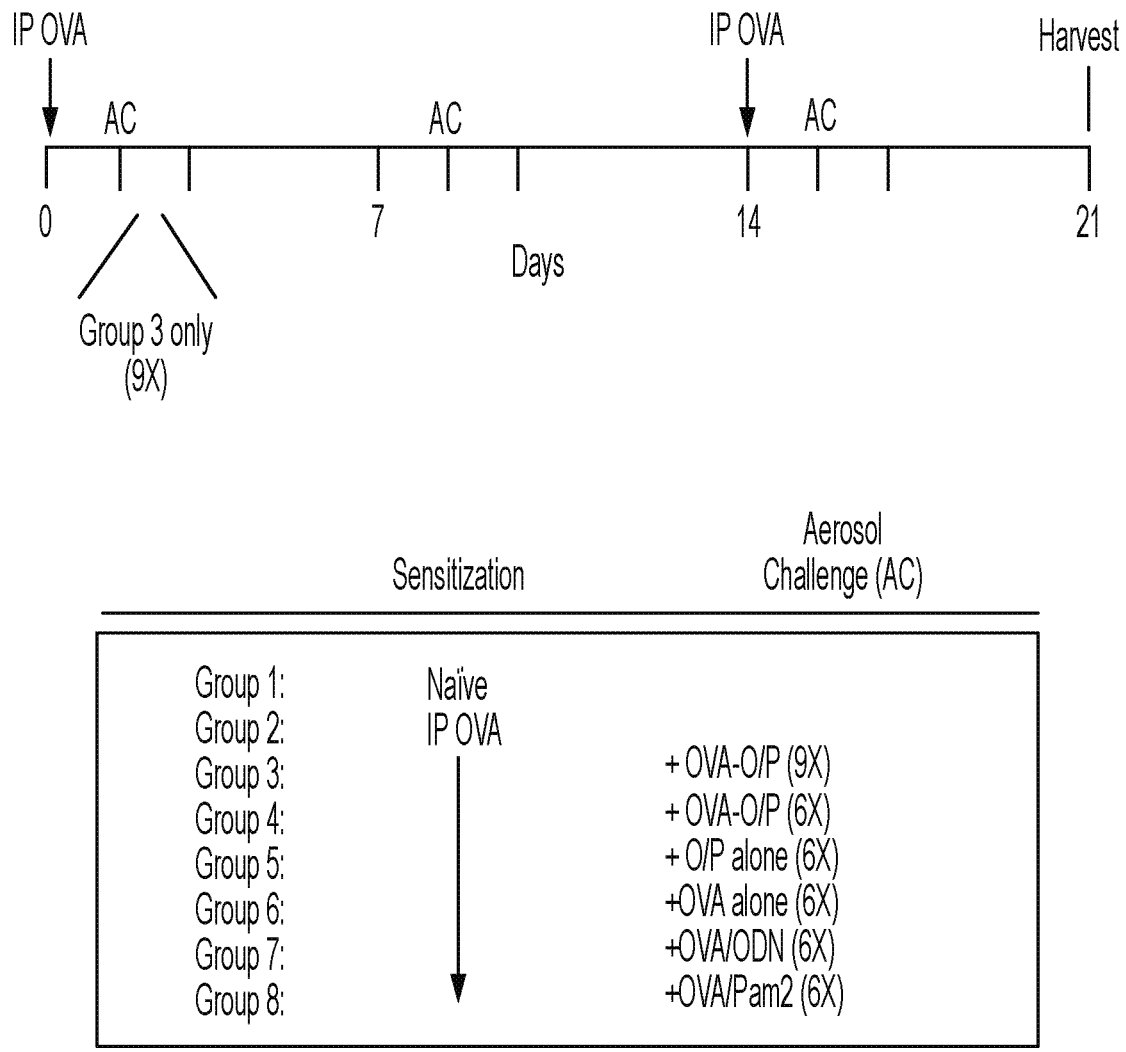
FIGS. 1A-1C. Aerosolized OVA-O/P dampens the allergic immune response.

Allergic asthma is a chronic respiratory disease associated with eosinophilic infiltration, increased mucus production, airway hyperresponsiveness (AHR), and airway remodeling (Barnes, *Nature Reviews Immunology* (2008), 8, 183-92). Despite recent advances in understanding the pathophysiology of asthma, some therapies still rely on general immune suppression by corticosteroids, which can have undesirable side effects, while short-acting drugs can provide immediate symptomatic relief but are still somewhat inadequate (Fanta, *N Engl J Med* (2009), 360:1002-14). Additional therapies are needed for treating allergic diseases.

The innate immune system provides immediate defense against invading pathogens (West et al., *Annu. Rev. Cell Dev. Biol.* (2006), 22:409-37; Ferrandon et al., *Nat Rev Immunol* (2007), 7:862-74). Over the past few years, several reports studying inducible innate resistance have revealed a robust ability of the lungs to significantly increase their innate immune defenses when stimulated with various Toll-like receptor (TLR) agonists (Evans et al., *Annu Rev Physiol* (2010), 72:413-35; Clement et al., *Am J Respir Crit Care Med* (2008), 177:1322-30; Evans et al., *Am J Respir Cell Mol Biol* (2010), 42:40-50; Tuvim et al., *PLoS ONE* (2009), 4:e4176). Up until recently, most work on immunity in mammals has focused on leukocytes because of their impressive array of antimicrobial functions. While it was known that mammalian epithelial cells, like those of insects, are capable of producing antimicrobial proteins, the relative importance of active epithelial defenses in mammals was poorly understood (Ferrandon et al., *Nat Rev Immunol* (2007), 7:862-74).

To gain a better understanding of the role of lung epithelial cells in influencing immune responses, investigators exposed mice to an aerosolized lysate of the bacterium non-typeable (unencapsulated) *Haemophilus influenzae* (NTHi), reasoning this would stimulate the epithelium with a mixture of pathogen-associated molecular patterns (PAMPs) in proportions reflecting a natural exposure (Clement et al., *Am J Respir Crit Care Med* (2008), 177:1322-30). This exposure triggered a high level of resistance to a broad array of microbial pathogens, and provided host protection as evidenced by increased microbial killing within the lungs (Clement et al., *Am J Respir Crit Care Med* (2008), 177: 1322-30). In subsequent studies, the lysate induced resistance to all pathogens tested, including Gram+ and Gram− bacteria, the spore-forming bioterror agent *B. anthracis*, the fungus *A. fumigatus*, and influenza virus (Evans et al., *Am J*

Respir Cell Mol Biol (2010), 42:40-50; Tuvim et al., *PLoS ONE* (2009) 4:e4176). Lastly, many studies have demonstrated that the epithelium itself plays a dominant role in providing this observed inducible resistance for the host (Ferrandon et al., *Nat Rev Immunol* (2007), 7:862-74; Evans et al., *Annu Rev Physiol* (2010), 72:413-35; Clement et al., *Am J Respir Crit Care Med* (2008), 177:1322-30; Evans et al., *Am J Respir Cell Mol Biol* (2010), 42:40-50; Tuvim et al., *PLoS ONE* (2009), 4:e4176; Mizgerd, *N Engl J Med* (2008), 358:716-27). Together, these studies support the concept that manipulation of airway epithelial innate immune defenses with TLR ligands may provide protection from other infections.

To determine necessary and sufficient stimuli and develop a chemically defined therapy, mice deficient in innate immune signaling components such as MyD88−/− and Trif−/− were examined (Duggan et al., *J Immunol* (2011), 186(10):5916-26; Evans et al., *Br J Pharmacol* (2011), 163:195-206). In contrast to the Trif−/− mice, resistance by a bacterial lysate could not be induced in MyD88−/− mice, indicating that a subset of TLRs were involved in mediating this response. To specifically identify which TLR ligands were involved, 15 TLR ligands covering TLR 1-9, including ligands with differential activity towards TLR 2/1 and 2/6 heterodimers, alone and in pairwise combinations were screened. Treatment with none of the single ligands improved mouse survival more than 20%. Certain combinations (e.g., TLR9+TLR2/6 agonist) improve survival more than 40%. In certain aspects treatment with a CpG oligodeoxynucleotide ("ODN", a TLR9 ligand) and Pam2CSK4 ("Pam2", a TLR2/6 ligand) resulted in a strong synergistic effect (Duggan et al., *J Immunol* (2011), 186(10): 5916-26). Mice pretreated with ODN/Pam2 survived challenges with *P. aeruginosa*, *S. pneumoniae*, or *K. pneumoniae*, in each case associated with a reduction in lung pathogen burden (Evans et al., *Br J Pharmacol* (2011), 163:195-206). These studies of the mechanism of inducible resistance have been complemented by studies of toxicity, biomarkers and dose-optimization (Evans et al., *Br J Pharmacol* (2011), 163:195-206).

I. ADAPTIVE IMMUNITY

The immune system is often divided into: (a) an innate immunity comprised of components that provide an immediate "first-line" of defense to continuously ward off pathogens and (b) an adaptive (acquired) immunity comprising the manufacture of antibodies and production or stimulation of T-cells specifically designed to target particular pathogens. Using adaptive immunity the body can develop over time a specific immunity to particular pathogen(s). This response takes days to develop, and so is not effective at preventing an initial invasion, but it will normally prevent any subsequent infection, and also aids in clearing up longer-lasting infections.

Two types of effector CD4+ T helper cell responses can be induced by antigen presenting cells (APC), designated Th1 and Th2, each designed to eliminate different types of pathogens. The factors that dictate whether an infection will trigger a Th1 or Th2 type response (type 1 or type 2 response) are not fully understood, but the response generated does play an important role in the clearance of different pathogens. The Th1 response is characterized by the production of Interferon-gamma, which activates the bactericidal activities of macrophages, and induces B cells to make opsonizing (coating) and complement-fixing antibodies, and leads to "cell-mediated immunity". The Th2 response is characterized by the release of Interleukin 4, which results in the activation of B cells to make neutralizing non-cytolytic antibodies, leading to "humoral immunity". Generally, Th1 responses are more effective against intracellular pathogens (viruses and bacteria that are inside host cells), while Th2 responses are more effective against extracellular bacteria, parasites including helminths and toxins. Like cytotoxic T cells, most of the CD4+ helper cells will die upon resolution of infection, with a few remaining as CD4+ memory cells.

II. IMMUNOMODULATORY COMPONENTS

Currently, allergic diseases and asthma are usually treated with one or more of the following drugs: (1) antihistamines and antileukotrienes, which antagonize the inflammatory mediators histamine and leukotrienes, (2) local or systemic (oral or injectable) corticosteroids, which suppress a broad spectrum of inflammatory mechanisms, and (3) short or long-acting bronchodilators, which relax smooth muscle of constricted airway in asthma. Long-term uses of systemic corticosteroids are known to cause many serious side effects and are advisable to avoid, if alternative therapies are available.

IgE, the IgE synthesis pathway, and the IgE-mediated allergic/inflammatory pathway are all important targets in intervening with the pathological processes of allergy and asthma. The B lymphocyte differentiation and maturation pathway that eventually generate IgE-secreting plasma cells go through the intermediate steps of IgE-expressing B lymphoblasts and involves the interaction with IgE-expressing memory B cells.

A. Allergens

In certain embodiments immunomodulating compositions include an allergen component or are administered in conjunction with an allergen component. An allergen component can include one or more of the following allergens or a derivative thereof that include, but are not limited to: microbes (e.g., bacteria, virus, fungi), pollens (e.g., farm plant, tree, weed, grass), animal danders, hymenoptera venoms, insects (e.g., house dust mites), plant foods, and animal foods.

The allergen can be selected from one or more types of mites, e.g., Mite, House Dust (*Dermatophagoides farinae*); Mite, House Dust (*Dermatophagoides pteronyssinus*); Mite, Food/Storage (*Acarus siro*); Mite, House Dust (*Blomia tropicalis*); Mite, Storage (*Chortoglyphus arcuates*); Mite, House Dust (*Euroglyphus maynei*); Mite, Food/Storage (*Lepidoglyphus destructor*); Mite, Food/Storage (*Tyrophagus putrescentiae*); and Mite, House Dust (*Glycyphagus domesticus*).

The allergen can be selected from one or more types of venoms, e.g., Bumble Bee Venom (*Bombus* spp.); European Hornet Venom (*Vespa crabro*); Honey Bee (*Apis mellifera*.); Mixed Hornet Venom (*Dolichovespula* spp); Mixed Paper Wasp Venom (*Polistes* spp.); Mixed Yellow Jacket Venom (*Vespula* spp.); White (bald)-faced Hornet Venom (*Dolichovespula maculate*); and Yellow Hornet Venom (*Dolichovespula arenaria*).

The allergen can be selected from one or more types of insects, e.g., Ant, Carpenter (*Camponotus pennsylvanicus*); Ant, Fire (*Solenopsis invicta*); Ant, Fire (*Solenopsis richteri*); Cockroach, American (*Periplaneta Americana*); Cockroach, German (*Blattella germanica*); Cockroach, Oriental (*Blatta orientalis*); Horse Fly (*Tabanus* spp.); House Fly (*Musca domestica*); Mayfly (*Ephemeroptera* spp.); Mosquito (*Culicidae* sp.); and Moth (*Heterocera* spp.).

The allergen can be selected from one or more types of epithelia, dander, and hair and feathers, e.g., Canary Feathers (*Serinus canaria*); Cat Epithelia (*Felis domesticus*)); Cattle Epithelia (*Bos Taurus*); Chicken Feathers (*Gallus gallas* (*domesticus*)); Dog Epithelia, Mixed Breeds (*Canis familiaris*); Duck Feathers (*Anal platyrhynchos*); Gerbil Epithelia (*Meriones unguiculatus*); Goat Epithelia (*Capra hircus*); Goose Feathers (*Anser domesticus*); Guinea Pig (*Cavia porcellus*); Epithelia ((*cobaya*)); Hamster Epithelia (*Mesocricetus auratus*); Hog Epithelia (*Sus scrofa*); Horse Epithelia (*Equus caballus*); Mouse Epithelia (*Mus musculus*); Parakeet Feathers (*Psittacidae* spp.); Pigeon Feathers (*Columba fasciata*); Rabbit Epithelia (*Oryctolagus cuniculus*); Rat Spithelia (*Rettus norvegicus*); and Wool, Sheep (*Ovis aries*).

The allergen can be selected from one or more types of dander, e.g., Cat dander/Antigen (*Felis catus* (*domesticus*)); Dog Dander, Mixed-Breed (*Canis familiaris*); and Poodle Dander (*Canis familiaris*).

The allergen can be selected from one or more types of fungi, e.g., Acremonium strictum; Alternaria alternate; Aspergillus amstelodami; Aspergillus flavus; Aspergillus furmigatus; Aspergillus nidulans; Aspergillus niger; Aspergillus terreus; Aspergillus versicolor; Aureohasidium Pullulans; Bipolaris sorokiniana; Botrytis cinerea; Candida albicans; Chaetomium globosum; Cladosporium herbarum; Cladosporium sphaerospermum; Drechslere spicifera; Epicoccum nigrum; Epidermophyton floccosum; Fusarium moniliforme; Fusarium solani; Geotrichum candidum; Gliocladium viride; Helminthosporium solani; Microsporum canis; Cephalosporium acremonium; Alternaria fermis; Aspergillus glaucus; Pullularia pullulans; Drechslera sorokiniana; Helminthosporium sativum; Hormodendrum hordei; Curvularia spicifera; Epicoccum purpurascens; Oospora lactic; Gliocladium deliquescens; Spondylocladium atrovirens; Microsporum lanosum; Mucor circinelloides f. circinelloides; Mucor circinelloides f lusitanicus; Muncor plumbeus; Mycogone perniciosa; Neurospora intermedia; Nigrospora oryzae; Paecilomyces variotii; Penicillium brevi-compactum; Penicillium camembertii; Penicillium chrysogenum; Penicillium digitatum; Penicillium expensum; Penicillium notatum; Penicillium roquefortii; Phoma betae; Phomma herbarum; Rhigopus oryzae; Rhizopus stolonifer; Rhodotorula mucilaginosa; Saccharomyces cerevisiae; Scopulariopsis brevicaulis; Serpula lacrymans; Setosphaeria rostrata; Stemphylium hotryosum; Stemphylium solani; Trichoderma harzianum; Trichophyton mentagrophytes; Trichophyton rubrum; Trichothecium roseum; Mucor mucedo; Mucor racemosus; Neurospora sitophil; Monilia sitophila; Phoma pigmentivora; Rhizopus arrhizus; Rhizopus nigricans; Rhodotorula rubra var. mucilaginosa; Merulius lacrymans; Exserohilum rostratum; Helminthosporium halodes; Trichoderma viride; Trichophyton interdigitale; and Cephalothecium roseum.

The allergen can be selected from one or more types of smuts, e.g., Barley Smut (*Ustilago nuda*); Bermuda Grass (*ustilago*); Smut (*cynodontis*); Corn Smut (*Ustilago maydis*); Johnson Grass (*Sporisorium*); Smut (*cruentum*); Oat Smut (*Ustilago avenae*); and Wheat Smut (*Ustilago tritici*).

The allergen can be selected from one or more types of grass pollens, e.g., Bahia (*Paspalum notalum*); Bermuda (*Cynodon dactylon*) Blue, Canada (*Poa compressa*); Brame, Smooth (*Bromus inermis*); Canary (*Phalaris arundinacea*); Corn (*Zea mays*); Couch/Quack (*Elytrigia repens* (*Agropyron repens*)); Johnson (*Sorghum halepense*); Kentucky Blue (*Poa pratensis*); Meadow Fescue (*Festuca pratensis* (*elatior*)); Oat, Cultivated (*Avena sativa*); Orchard (*Dactylis glomerata*); Red Top (*Agrostis gigantean* (*alba*)); Rye, Cultivated (*Secale cereale*); Rye, Giant Wild (*Leymus* (*Elymus*) condensatus); Rye, Italian (*Lolium perenne* ssp. *Multiflorum*); Rye, Perennial (*Lolium perenne*); Sweet Vernal (*Anthoxanehum odoratum*); Timothy (*Phleum pretense*); Velvet (*Holcus lanatus*); Wheat, Cultivated (*Triticum aestivum*); St. Augustine grass (*Stenotaphrum secundatum*), and Wheatgrass, Western (*Elymus* (*Agropyron*).

The allergen can be selected from one or more types of weed pollens, e.g., Allscale (*Atriplex polycarpa*); Baccharis (*Baccharis halimifolia*); Baccharis (*Baccharis sarothroides*); Burrobrush (*Hymenoclea salsola*); Careless Weed (*Amaranthus hybridus*); Cocklebur (*Xanthium strumarium* (*commune*)); Dock, Yellow (*Rumex crispus*); Dog Fennel (*Eupatorium capillifolium*); Goldenrod (*Solidago* spp.); Hemp, Western Water (*Amaranthus tuberculatus* (*Acnida tamariscina*)); Iodine Bush (*Allenrolfea occidentalis*); Jerusalem Oak (*Chenopodium botrys*); *Kochia*/Firebush (*Kochia scoparia*); Lambs Quarter (*Chenopodium album*); Marsh Elder, Burweed (*Iva xanthifolia*); Marsh Elder, Narrowleaf (*Iva angustifolia*); Marsh Elder, Rough (*Iva annua* (*ciliata*)); Mexican Tea (*Chenopodium ambrosioides*); Mugwort, Common (*Artemisia vulgaris*); Mugwort, Darkleaved (*Artemisia ludoviciana*); Nettle (*Urtica dioica*); Palmer's Amaranth (*Amaranthus palmeri*); Pigweed, Redroot/Rough (*Amaranthus retroflexus*); Pigweed, Spiny (*Amaranthus spinosus*); Plantain, English (*Plantago lanceolata*); Poverty Weed (*Iva axillaris*); Quailbrush (*Atriplex lentiformis*); Rabbit Bush (*Ambrosia deltoidea*); Ragweed, Desert (*Ambrosia dumosa*); Ragweed, False (*Ambrosia acanthicarpa*); Ragweed, Giant (*Ambrosia trifida*); Ragweed, Short (*Ambrosia artemisiifolia*); Ragweed, Slender (*Ambrosia confertiflora*); Ragweed, Southern (*Ambrosia bidentata*); Ragweed, Western (*Ambrosia psilostachya*); Russian Thistle (*Salsola kali* (pestifer)); Sage, Coastal (*Artemisia californica*); Sage, Pasture (*Artemisia frigida*); Sagebrush, Common (*Artemisia tridentate*); Saltbush, Annual (*Atriplex wrightii*); Shadscale (*Atriplex confertifolia*); Sorrel, Red/Sheep (*Rumex acetosella*); and Wingscale (*Atriplex canescens*); Wormwood, Annual (*Artemisia annua*).

The allergen can be selected from one or more types of tree pollens, e.g., Acacia (*Acacia* spp.); Alder, European (*Alnus glutinosa*); Alder, Red (*Alnus rubra*); Alder, Tag (*Alnus incana* ssp. *Rugosa*): Alder, White (*Alnus rhombifolia*); Ash, Arizona (*Fraxinus velutina*); Ash, Green/Red (*Fraxinus pennsylvanica*); Ash, Oregon (*Fraxinus latifolia*); Ash, White (*Fraxinus Americana*); Aspen (*Populus tremuloides*); Bayberry (*Myrica cerifera*); Beech, American (*Fagus grandifolia* (americana)) Beefwood/Australian Pine (*Casuarina equisetifolia*); Birch, Black/Sweet (*Betula lenta*); Birch, European White (*Betula pendula*); Birch, Red/River (*Betula nigra*); Birch, Spring (*Betula occidentalis* (*fontinalis*)); Birch, White (*Betula populifolia*); Box Elder (*Acer negundo*); Cedar, Japanese (*Cryptomeria japonica*); Cedar, Mountain (*Juniperus ashei* (sabinoides)); Cedar, Red (*Juniperus virginiana*); Cedar, Salt (*Tamarix gallica*); Cottonwood, Black (*Populus balsamifera* ssp. *Trichocarpa*); Cottonwood, Eastern (*Populus* deltoids); Cottonwood, Fremont (*Populus fremontii*); Cottonwood, Rio Grande (*Populus wislizeni*); Cottonwood, Western (*Populus* monilifera (*sargentii*)); Cypress, Arizona (*Cupressus arizonica*); Cypress, Bald (*Taxodium distichum*); Cypress, Italian (*Cupressus sempervirens*); Elm, American (*Ulmus Americana*); Elm, Cedar (*Ulmus crassifolia*); Elm, Siberian (*Ulmus pumila*); Eucalyptus (*Eucalyptus globulus*); Hackberry (*Celtis occidentalis*); Hazelnut (*Corylus Americana*); Hazelnut, European (*Corylus avellana*); Hickory, Pignut (*Carya glabra*); Hickory, Shagbark (*Carya ovata*); Hickory, Shellbark (*Carya laciniosa*); Hickory, White (*Carya alba*); Juniper, Oneseed (*Juniperus monosperma*); Juniper, Pinchot (*Juniperus pinchotii*); Juniper, Rocky Mountain (*Juniperus scopulorum*); Juniper, Utah (*Juniperus osteosperma*); Juniper, Western (*Juniperus occidentalis*); Locust Blossom, (*Robinia*); Black (*pseudoacacia*); Mango Blossom (*Mangifera indica*); Maple, Coast (*Acer macrophyllum*); Maple, Red (*Acer rubrum*); Maple, Silver (*Acer saccharinum*); Maple, Sugar (*Acer saccharum*); *Melaleuca* (*Melaleuca quinquenervia* (*leucadendron*)); Mesquite (*Prosopis glandulosa* (*julifiora*)); Mulberry, Paper (*Broussonetia papyrifera*); Mulberry, Red (*Morus rubra*); Mulberry, White (*Morus alba*); Oak, Arizona/Gambel (*Quercus gambeiji*); Oak, Black (*Quercus velutina*); Oak, Bur (*Quercus macrocarpa*); Oak, California Black (*Quercus kelloggii*); Oak, California Live (*Quercus agrifolia*); Oak, California White/Valley (*Quercus lobata*); Oak, English (*Quercus robur*); Oak, Holly (*Quercus ilex*); Oak, Post (*Quercus stellata*); Oak, Red (*Quercus rubra*); Oak, Scrub (*Quercus dumosa*); Oak, Virginia Live (*Quercus virginiana*); Oak, Water (*Quercus nigra*); Oak, Western White/Gany (*Quercus garryana*); Oak, White (*Quercus alba*); Olive (*Olea europaea*); Olive, Russian (*Elaeagnus angustifolia*); Orange Pollen (*Citrus sinensis*); Palm, Queen (*Arecastrum romanzoffianum* (*Cocos plumosa*)); Pecan (*Carya illinoensis*); Pepper Tree (*Schinus nolle*); Pepper Tree/Florida Holly (*Schinus terebinthifolius*); Pine, Loblolly (*Pinus taeda*); Pine, Eastern White (*Pinus strobus*); Pine, Longleaf (*Pinus palustris*); Pine, *Ponderosa* (*Pinus ponderosa*); Pine, Slash (*Pinus elliottii*); Pine, Virginia (*Pinus virginiana*); Pine, Western White (*Pinus monticola*); Pine, Yellow (*Pinus echinata*); Poplar, Lombardy (*Populus nigra*); Poplar, White (*Populus alba*) Privet (*Ligustrum vulgare*); Sweet Gum (*Liquidambar styraciflua*); Sycamore, Eastern (*Platanus occidentalis*); Sycamore, Oriental (*Platanus orientalis*); Sycamore, Western (*Platanus racemosa*); Sycamore/London Plane (*Platanus acerifolia*); Walnut, Black (*Juglans nigra*); Walnut, Calif. Black (*Juglans californica*); Walnut, English (*Juglans regia*); Willow, Arroyo (*Salix lasiolepis*); Willow, Black (*Salix nigra*); and Willow, Pussy (*Salix discolor*).

The allergen can be selected from one or more types of wild and cultivated flowers, e.g., Daisy, Ox-Eye (*Chrysanthemum leucanthemum*); Dandelion (*Taraxacum officinale*); and Sunflower (*Helianthus annuus*).

The allergen can be selected from one or more types of cultivated farm plant pollens, e.g., Alfalfa (*Medicago sativa*); Castor Bean (*Ricinus communis*); Clover, Red (*Trifolium pratense*); Mustard (*Brassica* spp.); and Sugar Beet (*Beta vulgaris*).

The allergen can be selected from one or more types of plant food, e.g., Almond (*Prunus dulcis*); Apple (*Malus pumila*); Apricot (*Prunus armeniaca*); Banana (*Musa paradisiaca* (*sapientum*)); Barley (*Hordeum vulgare*); Bean, Lima (*Phaseolus lunates*); Bean, Navy (*Phaseolus vulgaris*); Bean, Pinto (*Phaseolus* sp.) Bean, Red Kidney (*Phaseolus* sp.); Bean, String/Green (*Phaseolus vulgaris*); Blackberry (*Rubus allegheniensis*); Blueberry (*Vaccinium* sp.); Broccoli (*Brassica oleracea* var. *botrytis*); Buckwheat (*Fagopyrum esculentum*); Cabbage (*Brassica oleracea* var. *capitata*); Cacao Bean (*Theobroma cacao*); Cantaloupe (*Cucumis melo*); Carrot (*Daucus carota*); Cauliflower (*Brassica oleracea* var. *botrytis*); Celery (*Apium graveolens* var. *dulce*); Cherry (*Prunus* sp.); Cinnamon (*Cinnamomum verum*); Coffee (*Coffee Arabica*); Corn (*Zea mays*); Cranberry (*Vaccinium macrocarpon*); Cucumber (*Cucumis sativus*); Garlic (*Allium sativum*); Ginger (*Zingiber officinale*); Grape (*Vitis* sp.); Grapefruit (*Citrus paradise*); Hops (*Humulus lupulus*); Lemon (*Citrus limon*); Lettuce Malt (*Lactuca sativa*); Mushroom (*Agaricus campestris*); Mustard (*Brassica* sp.); Nutmeg (*Myristic fragrans*); Oat (*Avena sativa*); Olive, Green (*Olea europaea*); Onion (*Allium cepa* var. *cepa*); Orange (*Citrus sinensis*); Pea, Blackeye (*Vigna unguiculata*); Pea, Green (*Pisum sativum* (English)); Peach (*Prunus persica*); Pear (*Pyrus communis*); Pepper, Black (*Piper nigrum*); Pepper, Green (*Capsicum annuum* var. *annuum*); Pineapple (*Ananas comosus*); Potato, Sweet (*Ipomoea batatas*); Potato, White (*Solanum tuberosum*); Raspberry (*Rubus idaeus* var. *idaeus*); Rice (*Oryza sativa*); Rye (*Secale cereale*); Sesame Seed (*Sesamum orientale* (*indicum*)); Soybean (*Glycine max*); Spinach (*Spinacia oleracea*); Squash, Yellow (*Cucurbita pepo* var. *melopepo*); Strawberry (*Fraearia chiloensis*); Tomato (*Lycopersicon esculentum* (*lycopersicum*)); Turnip (*Brassica rapa* var. *rapa*); Vanilla Bean (*Vanilla planifolia*); Watermelon (*Citrullus lanatus* var. *lanatus*); and Wheat, Whole (*Triticum aestivum*).

The allergen can be selected from one or more types of fish and shellfish, e.g., Bass, Black (*Micropterus* sp.); Catfish (*Ictalurus punctatus*); Clam (*Mercenaria mercenaria*); Codfish (*Gadus morhua*); Crab (*Callinectes sapidus*); Flounder (*Platichthys* sp.); Halibut (*Hippoglossus* sp.); Lobster (*Homarus americanus*); Mackerel (*Scomber scombrus*); Oyster (*Crassostrea virginica*); Perch (*Sebastes marinus*); Salmon (*Salmo salar*); Sardine (*Clupeiformes*); Scallop (*Pectan magellanicus*); Shrimp (*Penaeus* sp.); Trout, Lake (*Salvelinus* sp.); and Tuna Fish (*Thunnus* sp.).

The allergen can be selected from one or more types of animal foods, e.g., Beef (*Bus Taurus*); Lamb (*Ovis aries*); and Pork (*Sus scrofa*).

The allergen can be selected from one or more types of poultry products, e.g., Chicken (*Gallus gallus*); Egg, Chicken, White (*Gallus gallus*); Egg, Chicken, Yolk (*Gallus gallus*); and Turkey (*Meleagris gallopavo*).

The allergen can be selected from one or more types of dairy products, e.g., Casein, bovine (*Bos Taurus*) and Milk, bovine (*Bos Taurus*).

The allergen can be selected from one or more types of nuts, e.g., Brazil Nut (*Bertholletia excelsa*); Cashew Nut (*Anacardium occidental*); Coconut (*Cocos nucifera*); Filbert/Hazelnut (*Corylus Americana*); Peanut (*Arachis hypogaea*); Pecan (*Carya illinoensis*); Walnut, Black (*Juglans nigra*); and Walnut, English (*Juglans regia*).

The allergen can be selected from one or more types of miscellaneous materials, e.g., latex, silver, or the like.

B. Inflammatory Diseases

There is a vast array of diseases exhibiting a chronic inflammatory component. These include but are not limited to: inflammatory joint diseases (e.g., rheumatoid arthritis, osteoarthritis, polyarthritis and gout), chronic inflammatory connective tissue diseases (e.g., lupus erythematosus, scleroderma, Sjorgen's syndrome, poly- and dermatomyositis, vasculitis, mixed connective tissue disease (MCTD), tendonitis, synovitis, bacterial endocarditis, osteomyelitis and psoriasis), chronic inflammatory lung diseases (e.g., chronic respiratory disease, pneumonia, fibrosing alveolitis, chronic bronchitis, chronic obstructive pulmonary disease (COPD), bronchiectasis, emphysema, silicosis and other pneumoconiosis and tuberculosis), chronic inflammatory bowel and gastro-intestinal tract inflammatory diseases (e.g., ulcerative colitis and Crohn's disease), chronic neural inflammatory diseases (e.g., chronic inflammatory demyelinating polyradiculoneuropathy, chronic inflammatory demyelinating polyneuropathy, multiple sclerosis, Guillan-Barre Syndrome and myasthenia gravis), other inflammatory diseases (e.g., mastitis, laminitis, laryngitis, chronic cholecystitis, Hashimoto's thyroiditis, inflammatory breast disease); chronic inflammation caused by an implanted foreign body in a wound; and acute inflammatory tissue damage due to muscle damage after eccentric exercise (e.g., delayed onset muscle soreness—DOMS). In certain aspects an inflammatory condition or disease is selected from the group consisting of, but not limited to chronic inflammatory lung diseases (e.g., chronic respiratory disease, pneumonia, fibrosing alveolitis, chronic bronchitis, chronic obstructive pulmonary disease (COPD), bronchiectasis, emphysema, silicosis and other pneumoconiosis and tuberculosis). In particular aspects the inflammatory disease is COPD.

The usual mode of treatment for chronic inflammatory conditions is by administration of non-steroidal anti-inflammatory drugs (NSAID's) such as Diclofenac, Ibuprofen, Aspirin, Phenylbutazone, Indomethacin, Naproxen and Piroxicam. Although NSAID's can be effective, they are known to be associated with a number of side effects and adverse reactions. These may include gastro-intestinal problems such as dyspepsia, ulceration and haemorrhage, sleepiness, nausea or vomiting, constipation, allergic reactions and occasionally hepatoxicity. Frequently the margin between effective dose and toxic dose is quite small (i.e., 2-3-fold). In spite of these side effects, the use of NSAID's as anti-inflammatory agents is standard practice in human medicine and veterinary medicine. However, within veterinary medicine there is an increasing concern about their use in food animals because of the potential for accumulation of drugs such as phenylbutazone within the food chain.

C. Toll-Like Receptor (TLR) Agonist

Toll-like receptors (TLRs) are highly conserved transmembrane proteins, consisting of an ectodomain with multiple leucine-rich repeats for pattern recognition, a membrane-spanning α-helix, and a Toll/interleukin-1 receptor (TIR) domain for intracellular signaling. At least 13 mammalian TLRs have been identified, each specifically localizing to either the plasma membrane or endosomal membranes, and each detects a unique complement of PAMPs (Akira et al., 2006; Shi et al., 2006). Upon PAMP recognition, signal transduction occurs via TLR-specific recruitment of cytosolic TIR adaptor protein combinations. In concert with one or more of the four other adaptors, the TIR adaptor protein MyD88 is required for signaling from most TLRs. The MyD88-independent signaling events observed from TLR3 and TLR4 require TIR adaptor TRIF (also known as TICAM-1), with or without participation of TRAM (Yamamoto et al., 2003). The TLR-specific TIR adaptor signaling cascade activates receptor-specific transcription factors, such as NF-κB, activating protein-1 and interferon regulatory factors (IRFs), leading to expression of inflammatory and antimicrobial genes (Akira et al., 2006; O'Neill, L. A., and Bowie, 2007; Takeda, K., and Akira, 2004).

A TLR agonist is any compound or substance that functions to activate a TLR directly, e.g., to induce a signaling event mediated by a TLR signal transduction pathway. Suitable TLR agonists include TLR1 agonists, TLR2 agonists, TLR3 agonists, TLR4 agonists, TLR5 agonists, TLR6 agonists, TLR7 agonists, TLR8 agonists, and TLR9 agonists. Specifically contemplated are compositions and methods specifically involving a TLR2/6 agonist in combination with a TLR9 agonist.

The term "agonist," as used herein, refers to a compound that can combine with a receptor (e.g., a TLR) to produce a cellular activity. An agonist may be a ligand that directly binds to the receptor. Alternatively, an agonist may combine with a receptor indirectly by, for example, (a) forming a complex with another molecule that directly binds to the receptor, or (b) otherwise results in the modification of another compound so that the other compound directly binds to the receptor. An agonist may be referred to as an agonist of a particular TLR (e.g., a TLR7 agonist) or a particular combination of TLRs (e.g., a TLR 7/8 agonist—an agonist of both TLR7 and TLR8).

The Terms

"TLR9 oligonucleotide agonist," "CpG-ODN," "CpG nucleic acid," "CpG polynucleotide," and "CpG oligonucleotide," used interchangeably herein, refer to a polynucleotide that stimulates or activates the TLR9 receptor. In particular, "CpG-ODN," "CpG nucleic acid," "CpG polynucleotide," and "CpG oligonucleotide," comprises at least one 5'-CG-3' moiety, and in many embodiments comprises an unmethylated 5'-CG-3' moiety. In general, a TLR9 oligonucleotide agonist is a single- or double-stranded DNA or RNA polynucleotide having at least six nucleotide bases that may comprise, or consist of, a modified nucleotide or a sequence of modified nucleosides. In some embodiments, the 5'-CG-3' moiety of the CpG nucleic acid is part of a palindromic nucleotide sequence. In some embodiments, the 5'-CG-3' moiety of the CpG nucleic acid is part of a non-palindromic nucleotide sequence. The TLR9 oligonucleotide can be an oligonucleotide analog.

Suitable TLR agonists include isolated, naturally-occurring TLR agonists; and synthetic TLR agonists. TLR agonists isolated from a naturally-occurring source of TLR agonist are generally purified, e.g., the purified TLR agonist is at least about 80% pure, at least about 90% pure, at least about 95% pure, at least about 98% pure, at least about 99% pure, or more than 99% pure. Synthetic TLR agonists are prepared by standard methods, and are generally at least about 80% pure, at least about 90% pure, at least about 95% pure, at least about 98% pure, at least about 99% pure, or more than 99% pure.

Suitable TLR agonists include TLR agonists that are not attached to any other compound. Suitable TLR agonists include TLR agonists that are attached, covalently or non-covalently, to a second compound. In some embodiments, a TLR agonist is attached to another compound directly. In other embodiments, a TLR agonist is attached to another compound through a linker. The compound to which a TLR agonist is attached includes a carrier, a scaffold, an insoluble support, a microparticle, a microsphere, and the like. Carriers include therapeutic polypeptides; polypeptides that provide for increased solubility; polypeptides that increase the half-life of the TLR agonist in a physiological medium (e.g., serum or other bodily fluid); and the like. In some embodiments, a TLR agonist will be conjugated, directly or via a linker, to a second TLR agonist.

In some embodiments, the TLR agonist is a prodrug version of a TLR agonist. Prodrugs are composed of a prodrug portion covalently linked to an active therapeutic agent. Prodrugs are capable of being converted to drugs (active therapeutic agents) in vivo by certain chemical or enzymatic modifications of their structure. Examples of prodrug portions are well-known in the art and can be found in the following references: Biological Approaches to the Controlled Delivery of Drugs, R. L. Juliano, New York Academy of Sciences, (1988); Hydrolysis in Drug and Prodrug Metabolism: Chemistry, Biochemistry, and Enzymology, Bernard Testa, Vch Verlagsgesellschaft Mbh, (2003); and Prodrugs: Topical and Ocular Drug Delivery, Kenneth Sloan, Marcel Dekker; (1992). Examples of prodrug portions are peptides, e.g., peptides that direct the TLR ligand to the site of action, and a peptide that possesses two or more free and uncoupled carboxylic acids at its amino terminus. Other exemplary cleaveable prodrug portions include ester groups, ether groups, acyl groups, alkyl groups, phosphate groups, sulfonate groups, N-oxides, and tert-butoxy carbonyl groups.

In some embodiments, the TLR agonist is a monomeric TLR agonist. In other embodiments, the TLR agonist is multimerized, e.g., the TLR agonist is polymeric. In some embodiments, a multimerized TLR agonist is homofunctional, e.g., is composed of one type of TLR agonist. In other embodiments, the multimerized TLR agonist is a heterofunctional TLR agonist.

In some embodiments, a TLR ligand is a chimeric TLR ligand (also referred to herein as a "heterofunctional" TLR ligand). In some embodiments, a chimeric TLR agonist comprises a TLR9 agonist moiety, and a TLR2 agonist moiety. The following are non-limiting examples of heterofunctional TLR agonists.

In some embodiments, a chimeric TLR ligand has the following formula: $(X)n-(Y)m$, where X is a TLR1 agonist, TLR2 agonist, TLR3 agonist, TLR4 agonist, TLR5 agonist, TLR6 agonist, TLR7 agonist, TLR8 agonist, and TLR9 agonist, and where Y is a TLR2 agonist, TLR3 agonist, TLR4 agonist, TLR5 agonist, TLR6 agonist, TLR7 agonist, TLR8 agonist, and TLR9 agonist, and n and m are independently an integer from 1, 2, 3, 4, 5, 6, 7, 8, 9, 10 or more including all values and ranges there between. In certain embodiments, X or Y is TLR9 and X or Y is TLR2/6.

TLR2 Agonists.

TLR2 agonists include isolated, naturally-occurring TLR2 agonists; and synthetic TLR2 agonists. TLR2 agonists isolated from a naturally-occurring source of TLR2 agonist are generally purified, e.g., the purified TLR2 agonist is at least about 80% pure, at least about 90% pure, at least about 95% pure, at least about 98% pure, at least about 99% pure, or more than 99% pure. Synthetic TLR2 agonists are prepared by standard means, and are generally at least about 80% pure, at least about 90% pure, at least about 95% pure, at least about 98% pure, at least about 99% pure, or more than 99% pure.

TLR2 agonists include TLR2 agonists that are not attached to any other compound. TLR2 agonists include TLR2 agonists that are attached, covalently or non-covalently, to a second compound. In some embodiments, a TLR2 agonist is attached to another compound directly. In other embodiments, a TLR2 agonist is attached to another compound through a linker.

TLR2 agonists include synthetic triacylated and diacylated lipopeptides. A non-limiting example of a TLR2 ligand is FSL-1 (a synthetic lipoprotein derived from *Mycoplasma salivarium* 1), Pam$_3$Cys (tripalmitoyl-S-glyceryl cysteine) or S-[2,3-bis(palmitoyloxy)-(2RS)-propyl]-N-palmitoyl-(R)-cysteine, where "Pam$_3$" is "tripalmitoyl-S-glyceryl") (Aliprantis et al., 1999). Derivatives of Pam$_3$Cys are also suitable TLR2 agonists, where derivatives include, but are not limited to, S-[2,3-bis(palmitoyloxy)-(2-R,S)-propyl]-N-palmitoyl-(R)-Cys-(S)-Ser-(Lys)$_4$ hydroxytrihydrochloride; Pam$_3$Cys-Ser-Ser-Asn-Ala; PaM$_3$Cys-Ser-(Lys)$_4$; Pam$_3$Cys-Ala-Gly; Pam$_3$Cys-Ser-Gly; Pam$_3$Cys-Ser; PaM$_3$Cys-OMe; Pam$_3$Cys-OH; PamCAG, palmitoyl-Cys ((RS)-2,3-di(palmitoyloxy)-propyl)-Ala-Gly-OH; and the like. Another non-limiting example of a suitable TLR2 agonist is Pam$_2$CSK$_4$ PaM$_2$CSK$_4$ (dipalmitoyl-S-glyceryl cysteine-serine-(lysine)$_4$; or Pam$_2$Cys-Ser-(Lys)$_4$) is a synthetic diacylated lipopeptide. Synthetic TLRs agonists have been described in the literature. See, e.g., Kellner et al. (1992); Seifer et al. (1990); Lee et al. (2003).

TLR3 Agonists.

TLR3 agonists include isolated, naturally-occurring TLR3 agonists; and synthetic TLR3 agonists. TLR3 agonists isolated from a naturally-occurring source of TLR3 agonist are generally purified, e.g., the purified TLR3 agonist is at least about 80% pure, at least about 90% pure, at least about 95% pure, at least about 98% pure, at least about 99% pure, or more than 99% pure. Synthetic TLR3 agonists are prepared by standard methods, and are generally at least about 80% pure, at least about 90% pure, at least about 95% pure, at least about 98% pure, at least about 99% pure, or more than 99% pure.

TLR3 agonists include TLR3 agonists that are not attached to any other compound. TLR3 agonists include TLR3 agonists that are attached, covalently or non-covalently, to a second compound. In some embodiments, a TLR3 agonist is attached to another compound directly. In other embodiments, a TLR3 agonist is attached to another compound through a linker.

TLR3 agonists include naturally-occurring double-stranded RNA (dsRNA); synthetic ds RNA; and synthetic dsRNA analogs; and the like (Alexopoulou et al., 2001). An exemplary, non-limiting example of a synthetic ds RNA analog is poly(I:C).

TLR4 Agonists.

Suitable TLR4 agonists include isolated, naturally-occurring TLR4 agonists; and synthetic TLR4 agonists. TLR4 agonists isolated from a naturally-occurring source of TLR4 agonist are generally purified, e.g., the purified TLR4 agonist is at least about 80% pure, at least about 90% pure, at least about 95% pure, at least about 98% pure, at least about 99% pure, or more than 99% pure. Synthetic TLR4 agonists are prepared by standard methods, and are generally at least about 80% pure, at least about 90% pure, at least about 95% pure, at least about 98% pure, at least about 99% pure, or more than 99% pure.

TLR4 agonists include TLR4 agonists that are not attached to any other compound. Suitable TLR4 agonists include TLR4 agonists that are attached, covalently or non-covalently, to a second compound. In some embodiments, a TLR4 agonist is attached to another compound directly. In other embodiments, a TLR4 agonist is attached to another compound through a linker. Suitable compounds to which a TLR4 agonist is attached include a carrier, a scaffold, and the like.

TLR4 agonists include naturally-occurring lipopolysaccharides (LPS), e.g., LPS from a wide variety of Gram negative bacteria; derivatives of naturally-occurring LPS; synthetic LPS; bacteria heat shock protein-60 (Hsp60); mannuronic acid polymers; flavolipins; teichuronic acids; *S. pneumoniae* pneumolysin; bacterial fimbriae, respiratory syncytial virus coat protein; and the like. TLR4 agonist also include monophosphoryl lipid A-synthetic (MPLAs, Invivogen) and Phosphorylated HexaAcyl Disaccharide (PHAD, Avanti Polar Lipids), as well as other synthetic TLR4 agonists.

TLR 5 Agonists.

Suitable TLR5 agonists include isolated, naturally-occurring TLR5 agonists; and synthetic TLR5 agonists. TLR5 agonists isolated from a naturally-occurring source of TLR5 agonist are generally purified, e.g., the purified TLR4 agonist is at least about 80% pure, at least about 90% pure, at least about 95% pure, at least about 98% pure, at least about 99% pure, or more than 99% pure. Synthetic TLR5 agonists are prepared by standard methods, and are generally at least about 80% pure, at least about 90% pure, at least about 95% pure, at least about 98% pure, at least about 99% pure, or more than 99% pure.

TLR5 agonists include TLR5 agonists that are not attached to any other compound. Suitable TLR5 agonists include TLR5 agonists that are attached, covalently or non-covalently, to a second compound. In some embodiments, a TLR5 agonist is attached to another compound directly. In other embodiments, a TLR5 agonist is attached to another compound through a linker. Suitable compounds to which a TLR5 agonist is attached include a carrier, a scaffold, and the like.

TLR5 agonists include a highly conserved 22 amino acid segment of flagellin as well as full length flagellin and other segments thereof.

TLR7 Agonists.

Suitable TLR7 agonists include isolated, naturally-occurring TLR7 agonists; and synthetic TLR7 agonists. TLR7 agonists isolated from a naturally-occurring source of TLR7 agonist are generally purified, e.g., the purified TLR7 agonist is at least about 80% pure, at least about 90% pure, at least about 95% pure, at least about 98% pure, at least about 99% pure, or more than 99% pure. Synthetic TLR7 agonists are prepared by standard means, and are generally at least about 80% pure, at least about 90% pure, at least about 95% pure, at least about 98% pure, at least about 99% pure, or more than 99% pure.

TLR7 agonists include TLR7 agonists that are not attached to any other compound. Suitable TLR7 agonists include TLR7 agonists that are attached, covalently or non-covalently, to a second compound. In some embodiments, a TLR7 agonist is attached to another compound directly. In other embodiments, a TLR7 agonist is attached to another compound through a linker.

TLR7 ligands include imidazoquinoline compounds; guanosine analogs; pyrimidinone compounds such as bropirimine and bropirimine analogs; and the like. Imidazoquinoline compounds that function as TLR7 ligands include, but are not limited to, imiquimod, (also known as Aldara, R-837, S-26308), and R-848 (also known as resiquimod, S-28463; having the chemical structure: 4-amino-2-ethoxymethyl-α,α-dimethyl-1H-imidazol[4,5-c]quinoli-ne-1-ethanol). Suitable imidazoquinoline agents include imidazoquinoline amines, imidazopyridine amines, 6,7-fused cycloalkylimidazopyridine amines, and 1,2 bridged imidazoquinoline amines. These compounds have been described in U.S. Pat. Nos. 4,689,338, 4,929,624, 5,238,944, 5,266,575, 5,268,376, 5,346,905, 5,352,784, 5,389,640, 5,395,937, 5,494,916, 5,482,936, 5,525,612, 6,039,969 and 6,110,929. Particular species of imidazoquinoline agents that are suitable for use in a subject method include R-848 (S-28463); 4-amino-2ethoxymethyl-α,α-dimethyl-1H-imi-dazo[4,5-c]quinoline-s-i-ethanol; and 1-(2-methylpropyl)-1H-imidazo[4,5-c]quinolin-4-amine (R-837 or Imiquimod). Also suitable for use is the compound 4-amino-2-(ethoxymethyl)-α,α-dimethyl-6,7,8,9-tetrahydro-1H-imidazo[4,5-c]quinoline-1-ethanol hydrate (see, e.g., BM-003 in Gorden et al. (2005).

Suitable compounds include those having a 2-aminopyridine fused to a five membered nitrogen-containing heterocyclic ring. Such compounds include, for example, imidazoquinoline amines including but not limited to substituted imidazoquinoline amines such as, for example, amide substituted imidazoquinoline amines, sulfonamide substituted imidazoquinoline amines, urea substituted imidazoquinoline amines, aryl ether substituted imidazoquinoline amines, heterocyclic ether substituted imidazoquinoline amines, amido ether substituted imidazoquinoline amines, sulfonamido ether substituted imidazoquinoline amines, urea substituted imidazoquinoline ethers, thioether substituted imidazoquinoline amines, and 6-, 7-, 8-, or 9-aryl or heteroaryl substituted imidazoquinoline amines; tetrahydroimidazoquinoline amines including but not limited to amide substituted tetrahydroimidazoquinoline amines, sulfonamide substituted tetrahydroimidazoquinoline amines, urea substituted tetrahydroimidazoquinoline amines, aryl ether substituted tetrahydroimidazoquinoline amines, heterocyclic ether substituted tetrahydroimidazoquinoline amines, amido ether substituted tetrahydroimidazoquinoline amines, sulfonamido ether substituted tetrahydroimidazoquinoline amines, urea substituted tetrahydroimidazoquinoline ethers, and thioether substituted tetrahydroimidazoquinoline amines; imidazopyridine amines including but not limited to amide substituted imidazopyridine amines, sulfonamido substituted imidazopyridine amines, urea substituted imidazopyridine amines, aryl ether substituted imidazopyridine amines, heterocyclic ether substituted imidazopyridine amines, amido ether substituted imidazopyridine amines, sulfonamido ether substituted imidazopyridine amines, urea substituted imidazopyridine ethers, and thioether substituted imidazopyridine amines; 1,2-bridged imidazoquinoline amines; 6,7-fused cycloalkylimidazopyridine amines; imidazonaphthyridine amines; tetrahydroimidazonaphthyridine amines; oxazoloquinoline amines; thiazoloquinoline amines; oxazolopyridine amines; thiazolopyridine amines; oxazolonaphthyridine amines; thiazolonaphthyridine amines; and 1H-imidazo dimers fused to pyridine amines, quinoline amines, tetrahydroquinoline amines, naphthyridine amines, and tetrahydronaphthyridine amines.

Compounds include a substituted imidazoquinoline amine, a tetrahydroimidazoquinoline amine, an imidazopyridine amine, a 1,2-bridged imidazoquinoline amine, a 6,7-fused cycloalkylimidazopyridine amine, an imidazonaphthyridine amine, a tetrahydroimidazonaphthyridine amine, an oxazoloquinoline amine, a thiazoloquinoline amine, an oxazolopyridine amine, a thiazolopyridine amine, an oxazolonaphthyridine amine, and a thiazolonaphthyridine amine.

As used herein, a substituted imidazoquinoline amine refers to an amide substituted imidazoquinoline amine, a sulfonamide substituted imidazoquinoline amine, a urea substituted imidazoquinoline amine, an aryl ether substituted imidazoquinoline amine, a heterocyclic ether substituted imidazoquinoline amine, an amido ether substituted imidazoquinoline amine, a sulfonamido ether substituted imidazoquinoline amine, a urea substituted imidazoquinoline ether, a thioether substituted imidazoquinoline amines, or a 6-, 7-, 8-, or 9-aryl or heteroaryl substituted imidazoquinoline amine.

Guanosine analogs that function as TLR7 ligands include certain C8-substituted and N7, C8-disubstituted guanine ribonucleotides and deoxyribonucleotides, including, but not limited to, Loxoribine (7-allyl-8-oxoguanosine), 7-thia-8-oxo-guanosine (TOG), 7-deazaguanosine, and 7-deazadeoxyguanosine (Lee et al., 2003). Bropirimine (PNU-54461), a 5-halo-6-phenyl-pyrimidinone, and bropirimine analogs are described in the literature and are also suitable for use. See, e.g., Vroegop et al. (1999). Additional examples of suitable C8-substituted guanosines include but are not limited to 8-mercaptoguanosine, 8-bromoguanosine, 8-methylguanosine, 8-oxo-7,8-dihydroguanosine, C8-arylamino-2'- deoxyguanosine, C8-propynyl-guanosine, C8- and N7-substituted guanine ribonucleosides such as 7-allyl-8-oxoguanosine (loxoribine) and 7-methyl-8-oxoguanosine, 8-aminoguanosine, 8-hydroxy-2'-deoxyguanosine, and 8-hydroxyguanosine.

In some embodiments a substituted guanine TLR7 ligand is monomeric. In other embodiments, a substituted guanine TLR7 ligand is multimeric. Thus, in some embodiments, a TLR7 ligand has the formula: (B)q, where B is a substituted guanine TLR7 ligand, and q is 1, 2, 3, 4, 5, 6, 7, 8, 9, or 10. The individual TLR7 ligand monomers in a multimeric TLR7 ligand are linked, covalently or non-covalently, either directly to one another or through a linker. Suitable TLR7 agonists include a TLR7 ligand as described in U.S. Patent Publication 2004/0162309.

In some embodiments, a TLR7 agonist is a selective TLR7 agonist, e.g., the agonist modulates cellular activity through TLR7, but does not modulate cellular activity through TLR8. TLR7-selective agonists include those shown in U.S. Patent Publication 2004/0171086. Such TLR7 selective agonist compounds include, but are not limited to, $N^1$-{4-[4-amino-2-(2-methoxyethyl)-6,7,8,9-tetrahydro-1H-imidazo[4,5-c]quinolin-1-yl]butyl}-4-fluoro-1-benzenesulfonamide, $N^1$-[4-(4-amino-2-(2-methoxyethyl)-1H-imidazo[4,5-c]quinolin-1-yl)butyl]-4-fluoro-1-benzenesulfonamide, N-[4-(4-amino-2-propyl-1H-imidazo[4,5-c]quinolin-1-yl)butyl]methanesulfonamide, N-{3-[4-amino-2-(2-methoxyethyl)-1H-imidazo[4,5-c]quinolin-1-yl]-2,2-dimethylpropyl}benzamide, N-(2-{2-[4-amino-2-(2-methoxyethyl)-1H-imidazo[4,5-c]quinolin-1-yl]ethoxy}ethyl)-N-methylmethanesulfonamide, N-(2-{2-[4-amino-2-(2-methoxyethyl)-6,7,8,9-tetrahydro-1H-imidazo[4,5-c]quinolin-1-yl]ethoxy}ethyl)benzamide, N-[4-(4-amino-2-methyl-1H-imidazo[4,5-c]quinolin-1-yl)butyl]cyclopentanecarboxamide, 1-[4-(1,1-dioxidoisothiazolidin-2-yl)butyl]-2-(2-methoxyethyl)-1H-imidazo[4,5-c]quinolin-4-amine, 2-methyl-1-[5-methyl sulfonyl)pentyl-6,7,8,9-tetrahydro-1H-imidazo[4,5-c]quinolin-4-amine, N-{2-[4-amino-2-(ethoxymethyl)-6,7-dimethyl-1H-imidazo[4,5-c]pyridin-1-yl]-1,1-dimethylethyl}-N-cyclohexylurea, N-[2-(4-amino-2-ethyl-1H-imidazo[4,5-c]quinolin-1-yl)-1,1-dimethylethyl]benzamide, N-[3-(4-amino-2-butyl-1H-imidazo[4,5-c]quinolin-1-yl)-2,2-dimethylpropyl]methanesulfonamide, 1-[6-(methanesulfonyl)hexyl]-6,7-dimethyl-2-propyl-1H-imidazo[4,5-c]pyridin-4-amine, 6-(6-amino-2-propyl-1H-imidazo[4,5-c]quinolin-1-yl)-N-methoxy-N-methylhexamide, 1-[2,2-dimethyl-3-(methyl sulfonyl)propyl]-2-(ethoxymethyl)-1H-imidazo[4,5-c]quinolin-4-amine, N-[4-(4-amino-2-methyl-1H-imidazo[4,5-c]quinolin-1-yl)butyl]-N-methyl-N-phenylurea, 1-{3-[4-amino-1-(2-methylpropyl)-1H-imidazo[4,5-c]quinolin-8-yl]phenyl}ethanone, 7-(4-amino-2-propyl-1H-imidazo[4,5-c]quinolin-1-yl)-2-methylheptan-2-ol, N-methyl-4-(4-amino-2-ethyl-1H-imidazo[4,5-c]quinolin-1-yl)butane-1-sulfonamide, N-(4-methoxybenzyl)-4-(4-amino-2-ethyl-1H-imidazo[4,5-c]quinolin-1-yl)butane-1-sulfonamide, N-{2-[4-amino-3-(ethoxymethyl)-6,7-dimethyl-1H-imidazo[4,5-c]pyridin-1-yl]-1,1-dimethylethyl}methanesulfonamide, 2-ethoxymethyl-1-(3-methoxypropyl)-7-(5-hydroxymethylpyridin-3-yl)-1H-imidazo[4,5-c]quinolin-4-amine, 1-[(2,2-dimethyl-1,3-dioxolan-4-yl)methyl]-2-(ethoxymethyl)-7-(pyridin-3-yl)-1H-imidazo[4,5-c]quinolin-4-amine, 4-[3-(4-amino-6,7-dimethyl-2-propyl-1H-imithizo[4,5-c]pyridin-1-yl)propane-1-sulfonyl]-benzoic acid ethyl ester, 2-butyl-1-{2-[2-(methyl sulfonyl)ethoxy]ethyl}-1H-imidazo[4,5-c]quinolin-4-amine, N-(2-{4-amino-2-ethoxymethyl-7-[6-(methanesulfonylamino)hexyloxy]-1H-imidazo[4,5-c]quinolin-1-yl}-1,1-dimethylethyl)methanesulfonamide, N-(6-{[4-amino-2-ethoxymethyl-1-(2-methanesulfonylamino-2-methylpropyl)-1H-imidazo[4,5-c]quinolin-7-yl]oxy}hexyl)acetamide, 1-[4-(1,1-dioxidoisothiazolidin-2-yl)butyl]-2-ethoxymethyl-7-(pyridin-3-yl)-1H-imidazo[4,5-c]quinolin-4-amine, 1-[4-(1,1-dioxidoisothiazolidin-2-yl)butyl]-2-ethoxymethyl-7-(pyridin-4-yl)-1H-imidazo[4,5-c]quinolin-4-amine, 1-[4-(1,1-dioxidoisothiazolidin-2-yl)butyl]-2-ethoxymethyl-7-phenyl-1H-imidazo[4,5-c]quinolin-4-amine, 2-(ethoxymethyl)-1-{[1-(methyl sulfonyl)piperidin-4-yl]methyl}-7-(pyridin-3-yl)-1H-imidazo[4,5-c]quinolin-4-amine, 2-(ethoxymethyl)-1-[(1-isobutyrylpiperidin-4-yl)methyl]-7-(pyridin-3-yl)-1H-imidazo[4,5-c]quinolin-4-amine, 2-(ethoxymethyl)-1-{[1-(morpholic-4-ylcarbonyl)piperidin-4-yl]methyl}-7-(pyridin-3-yl)-1H-imidazo[4,5-c]quinolin-4-amine, Cyclopropanecarboxylic acid [3-(4-amino-2-propyl-1H-imidazo[4,5-c]quinolin-1-yl)propoxy]amide, Isopropylcarbamic acid 4-amino-2-(2-methoxyethyl)-1-propyl-1H-imidazo[4,5-c]quinolin-7-yl ester, Ethyl 4-(4-amino-2-propyl-1H-imidazo[4,5-c]quinolin-1-yl)butyrate, 1-[4-amino-2-ethyl-7-(pyridin-3-yl)-1H-imidazo[4,5-c]quinolin-1-yl]-2-methylpropan-2-ol, 1-(4-amino-2-ethyl-7-[5-{hydroxymethyl)pyridin-3-yl]-1H-imidazo[4,5-c]quinolin-1-yl}-2-methylpropan-2-ol, 1-(3-[4-amino-2-(2-methoxyethyl)-8-(pyridin-3-yl)-1H-imidazo[4,5-c]quinolin-1-yl]propyl]pyrolidin-2-one, N-(2-{4-amino-2-ethoxymethyl-7-[6-(methanesulfonylamino)hexyloxy]-1H-imidazo[4,5-c]quinolin-1-yl}-1,1-dimethylethyl)acetamide, 1-{3-[4-amino-7-(3-hydroxymethylphenyl)-2-(2-methoxyethyl)-1H-imidazo[4,5-c]quinolin-1-yl]propyl}pyrrolidin-2-one, N-{4-[4-amino-2-ethoxymethyl-7-(pyridin-3-yl)-1H-imidazo[4,5-c]quinolin-1-yl]butyl}-N-propylurea, N-{4-[4-amino-2-ethoxymethyl-7-(pyridin-3-yl)-1H-imidazo[4,5-c]quinolin-1-yl]butyl}butyramide, 5-(4-amino-2-propyl-1H-imidazo[4,5-c]quinolin-1-yl)-4,4-dimethylpentan-2-one, 1-cyclohexylmethyl-2-ethoxymethyl-7-(5-hydroxymethylpyridin-3-yl)-1H-imidazo[4,5-c]quinolin-4-amine, N,N-dimethyl-5-(4-amino-2-ethoxymethyl-1H-imidazo[4,5-c]quinolin-1-yl)pentane-1-sulfonamide, N-{3-[(4-amino-2-ethoxymethyl-1H-imidazo[4,5-c]quinolin-1-yl)amino]propyl}methanesulfonamide, and/or N,N-dimethyl-4-(4-amino-2-ethoxymethyl-1H-imidazo[4,5-c]quinolin-1-yl)butane-1-sulfonamide.

Additional suitable TLR7 selective agonists include, but are not limited to, 2-(ethoxymethyl)-1-(2-methylpropyl)-1H-imidazo[4,5-c]quinolin-4-amine (U.S. Pat. No. 5,389,640); 2-methyl-1-[2-(3-pyridin-3-ylpropoxy)ethyl]-1H-imidazo[4,5-c]quinolin-4-amine (WO 02/46193); N-(2-{2-[4-amino-2-(2-methoxyethyl)-1H-imidazo[4,5-c]quinolin-1-yl]ethoxy} ethyl)-N-methylcyclohexanecarboxamide (U.S. Patent Publication 2004/0171086); 1-[2-(benzyloxy)ethyl]-2-methyl-1H-imidazo[4,5-c]quinolin-4-amine (WO 02/46189); N-{8-[4-amino-2-(2-methyoxyethyl)-1H-imidazo[4,5-c]quinolin-1-yl]octyl}-N-phenylurea (U.S. Patent Publication 2004/0171086 (IRM5)); 2-butyl-1-[5-(methylsulfonyl)pentyl]-1H-imidazo[4,5-c]quinolin-4-amine (WO 02/46192); N-{3-[4-amino-2-(2-methoxyethyl)-1H-imidazo[4,5-c]quinolin-1-yl]propyl}-4-methylbenzenesulfonamide (U.S. Pat. No. 6,331,539); and N-[4-(4-amino-2-ethyl-1H-imidazo[4,5-c]quinolin-1-yl)butyl]cyclohexanecar-boxamide (U.S. Patent Publication 2004/0171086 (IRM8)). Also suitable for use is the TLR7-selective agonist N-[4-(4-amino-2-ethyl-1H-imidazo[4,5-c]quinolin-1-yl)butyl-]methanesulfon-amide (Gorden et al., 2005).

TLR8 Agonists.

Suitable TLR8 agonists include isolated, naturally-occurring TLR8 agonists; and synthetic TLR8 agonists. TLR8 agonists isolated from a naturally-occurring source of TLR8 agonist are generally purified, e.g., the purified TLR8 agonist is at least about 80% pure, at least about 90% pure, at least about 95% pure, at least about 98% pure, at least about 99% pure, or more than 99% pure. Synthetic TLR8 agonists are prepared by standard methods, and are generally at least about 80% pure, at least about 90% pure, at least about 95% pure, at least about 98% pure, at least about 99% pure, or more than 99% pure.

TLR8 agonists include TLR8 agonists that are not attached to any other compound. TLR8 agonists include TLR8 agonists that are attached, covalently or non-covalently, to a second compound. In some embodiments, a TLR8 agonist is attached to another compound directly. In other embodiments, a TLR8 agonist is attached to another compound through a linker.

TLR8 agonists include, but are not limited to, compounds such as R-848, and derivatives and analogs thereof. Suitable TLR8 agonists include compounds having a 2-aminopyridine fused to a five membered nitrogen-containing heterocyclic ring. Such compounds include, for example, imidazoquinoline amines including but not limited to substituted imidazoquinoline amines such as, for example, amide substituted imidazoquinoline amines, sulfonamide substituted imidazoquinoline amines, urea substituted imidazoquinoline amines, aryl ether substituted imidazoquinoline amines, heterocyclic ether substituted imidazoquinoline amines, amido ether substituted imidazoquinoline amines, sulfonamido ether substituted imidazoquinoline amines, urea substituted imidazoquinoline ethers, thioether substituted imidazoquinoline amines, and 6-, 7-, 8-, or 9-aryl or heteroaryl substituted imidazoquinoline amines; tetrahydroimidazoquinoline amines including but not limited to amide substituted tetrahydroimidazoquinoline amines, sulfonamide substituted tetrahydroimidazoquinoline amines, urea substituted tetrahydroimidazoquinoline amines, aryl ether substituted tetrahydroimidazoquinoline amines, heterocyclic ether substituted tetrahydroimidazoquinoline amines, amido ether substituted tetrahydroimidazoquinoline amines, sulfonamido ether substituted tetrahydroimidazoquinoline amines, urea substituted tetrahydroimidazoquinoline ethers, and thioether substituted tetrahydroimidazoquinoline amines; imidazopyridine amines including but not limited to amide substituted imidazopyridine amines, sulfonamide substituted imidazopyridine amines, urea substituted imidazopyridine amines, aryl ether substituted imidazopyridine amines, heterocyclic ether substituted imidazopyridine amines, amido ether substituted imidazopyridine amines, sulfonamido ether substituted imidazopyridine amines, urea substituted imidazopyridine ethers, and thioether substituted imidazopyridine amines; 1,2-bridged imidazoquinoline amines; 6,7-fused cycloalkylimidazopyridine amines; imidazonaphthyridine amines; tetrahydroimidazonaphthyridine amines; oxazoloquinoline amines; thiazoloquinoline amines; oxazolopyridine amines; thiazolopyridine amines; oxazolonaphthyridine amines; thiazolonaphthyridine amines; and 1H-imidazo dimers fused to pyridine amines, quinoline amines, tetrahydroquinoline amines, naphthyridine amines, or tetrahydronaphthyridine amines.

In one particular embodiment, the TLR8 agonist is an amide substituted imidazoquinoline amine. In an alternative embodiment, the TLR8 agonist is a sulfonamide substituted imidazoquinoline amine. In another alternative embodiment, the TLR8 agonist is a urea substituted imidazoquinoline amine. In another alternative embodiment, the TLR8 agonist is an aryl ether substituted imidazoquinoline amine. In another alternative embodiment, the TLR8 agonist is a heterocyclic ether substituted imidazoquinoline amine. In another alternative embodiment, the TLR8 agonist is an amido ether substituted imidazoquinoline amine. In another alternative embodiment, the TLR8 agonist is a sulfonamido ether substituted imidazoquinoline amine. In another alternative embodiment, the TLR8 agonist is a urea substituted imidazoquinoline ether. In another alternative embodiment, the TLR8 agonist is a thioether substituted imidazoquinoline amine. In another alternative embodiment, the TLR8 agonist is a 6-, 7-, 8-, or 9-aryl or heteroaryl substituted imidazoquinoline amine.

In another alternative embodiment, the TLR8 agonist is an amide substituted tetrahydroimidazoquinoline amine. In another alternative embodiment, the TLR8 agonist is a sulfonamide substituted tetrahydroimidazoquinoline amine. In another alternative embodiment, the TLR8 agonist is a urea substituted tetrahydroimidazoquinoline amine.

In another alternative embodiment, the TLR8 agonist is an aryl ether substituted tetrahydroimidazoquinoline amine. In another alternative embodiment, the TLR8 agonist is a heterocyclic ether substituted tetrahydroimidazoquinoline amine. In another alternative embodiment, the TLR8 agonist is an amido ether substituted tetrahydroimidazoquinoline amine. In another alternative embodiment, the TLR8 agonist is a sulfonamido ether substituted tetrahydroimidazoquinoline amine. In another alternative embodiment, the TLR8 agonist is a urea substituted tetrahydroimidazoquinoline ether. In another alternative embodiment, the TLR8 agonist is a thioether substituted tetrahydroimidazoquinoline amine.

In another alternative embodiment, the TLR8 agonist is an amide substituted imidazopyridine amines. In another alternative embodiment, the TLR8 agonist is a sulfonamide substituted imidazopyridine amine. In another alternative embodiment, the TLR8 agonist is a urea substituted imidazopyridine amine. In another alternative embodiment, the TLR8 agonist is an aryl ether substituted imidazopyridine amine. In another alternative embodiment, the TLR8 agonist is a heterocyclic ether substituted imidazopyridine amine. In another alternative embodiment, the TLR8 agonist is an amido ether substituted imidazopyridine amine. In another alternative embodiment, the TLR8 agonist is a sulfonamido ether substituted imidazopyridine amine. In another alternative embodiment, the TLR8 agonist is a urea substituted imidazopyridine ether. In another alternative embodiment, the TLR8 agonist is a thioether substituted imidazopyridine amine.

In another alternative embodiment, the TLR8 agonist is a 1,2-bridged imidazoquinoline amine. In another alternative embodiment, the TLR8 agonist is a 6,7-fused cycloalkylimidazopyridine amine.

In another alternative embodiment, the TLR8 agonist is an imidazonaphthyridine amine. In another alternative embodiment, the TLR8 agonist is a tetrahydroimidazonaphthyridine amine. In another alternative embodiment, the TLR8 agonist is an oxazoloquinoline amine. In another alternative embodiment, the TLR8 agonist is a thiazoloquinoline amine. In another alternative embodiment, the TLR8 agonist is an oxazolopyridine amine. In another alternative embodiment, the TLR8 agonist is a thiazolopyridine amine. In another alternative embodiment, the TLR8 agonist is an oxazolonaphthyridine amine. In another alternative embodiment, the TLR8 agonist is a thiazolonaphthyridine amine.

In yet another alternative embodiment, the TLR8 agonist is a 1H-imidazo dimer fused to a pyridine amine, quinoline amine, tetrahydroquinoline amine, naphthyridine amine, or a tetrahydronaphthyridine amine.

In some embodiments, the TLR8 agonist is a selective TLR8 agonist, e.g., the agonist modulates cellular activity through TLR8, but does not modulate cellular activity through TLR7. TLR8-selective agonists include those in U.S. Patent Publication 2004/0171086. Such TLR8 selective agonist compounds include, but are not limited to, the compounds shown in U.S. Patent Publication No. 2004/0171086 that include N-{4-[4-amino-2-(2-methoxyethyl)-1H-imidazo[4,5-c]quinolin-1-yl]butyl}quinolin-3-carboxamide, N-{4-[4-amino-2-(2-methoxyethyl)-1H-imidazo[4,5-c]quinolin-1-yl]butyl}quinoxoline-2-carboxamide, and N-[4-(4-amino-2-propyl-1H-imidazo[4,5-c]quinolin-1-yl)butyl]morpholine-4-carboxamide.

Other suitable TLR8-selective agonists include, but are not limited to, 2-propylthiazolo[4,5-c]quinolin-4-amine (U.S. Pat. No. 6,110,929); $N^1$-[2-(4-amino-2-butyl-1H-imidazo[4,5-c][1,5]naphthridin-1-yl)ethyl]-2-amino-4-methylpentanamide (U.S. Pat. No. 6,194,425); $N^1$-[4-(4-amino-1H-imidazo[4,5-c]quinolin-1-yl)butyl]-2-phenoxy-benzamide (U.S. Pat. No. 6,451,810); $N^1$-[2-(4-amino-2-butyl-1H-imidazo[4,5-c]quinolin-1-yl)ethyl]-1-propa-nesulfonamide (U.S. Pat. No. 6,331,539); N-{2-[2-(4-amino-2-ethyl-1H-imidazo[4,5-c]quinolin-1-yl)ethyoxy]ethyl}-N'-phenylurea (U.S. Patent Publication 2004/0171086); 1-{4-[3,5-dichlorophenyl)thio]butyl}-2-ethyl-1H-imidazo[4,5-c]quinolin-4-amine (U.S. Patent Publication 2004/0171086); N-{2-[4-amino-2-(ethoxymethyl)-1H-imidazo[4,5-c]quinolin-1-yl]ethyl}-N'-(3-cyanophenyl) urea (WO 00/76518 and U.S. Patent Publication No. 2004/0171086); and 4-amino-α,α-dimethyl-2-methoxyethyl-1H-imidazo[4,5-c]quinoli-ne-1-ethanol (U.S. Pat. No. 5,389,640). Included for use as TLR8-selective agonists are the compounds in U.S. Patent Publication No. 2004/0171086. Also suitable for use is the compound 2-propylthiazolo-4,5-c]quinolin-4-amine (Gorden et al., 2005 supra).

TLR9 Agonists.

Suitable TLR9 agonists include isolated, naturally-occurring TLR9 agonists; and synthetic TLR9 agonists. TLR9 agonists isolated from a naturally-occurring source of TLR9 agonist are generally purified, e.g., the purified TLR9 agonist is at least about 80% pure, at least about 90% pure, at least about 95% pure, at least about 98% pure, at least about 99% pure, or more than 99% pure. Synthetic TLR9 agonists are prepared by standard methods, and are generally at least about 80% pure, at least about 90% pure, at least about 95% pure, at least about 98% pure, at least about 99% pure, or more than 99% pure.

TLR9 agonists include TLR9 agonists that are not attached to any other compound. TLR9 agonists include TLR9 agonists that are attached, covalently or non-covalently, to a second compound. In some embodiments, a TLR9 agonist is attached to another compound directly. In other embodiments, a TLR9 agonist is attached to another compound through a linker.

Examples of TLR9 agonists (also referred to herein as "TLR9 ligands") include nucleic acids comprising the sequence 5'-CG-3' (a "CpG nucleic acid" or "ODN"), in certain aspects C is unmethylated. The terms "polynucleotide," and "nucleic acid," as used interchangeably herein in the context of TLR9 ligand molecules, refer to a polynucleotide of any length, and encompasses, inter alia, single- and double-stranded oligonucleotides (including deoxyribonucleotides, ribonucleotides, or both), modified oligonucleotides, and oligonucleosides, alone or as part of a larger nucleic acid construct, or as part of a conjugate with a non-nucleic acid molecule such as a polypeptide. Thus a TLR9 ligand may be, for example, single-stranded DNA (ssDNA), double-stranded DNA (dsDNA), single-stranded RNA (ssRNA) or double-stranded RNA (dsRNA). TLR9 ligands also encompasses crude, detoxified bacterial (e.g., mycobacterial) RNA or DNA, as well as enriched plasmids enriched for a TLR9 ligand. In some embodiments, a "TLR9 ligand-enriched plasmid" refers to a linear or circular plasmid that comprises or is engineered to comprise a greater number of CpG motifs than normally found in mammalian DNA. Three types of stimulatory CpG ODNs have been identified, types A, B and C, which differ in their immunestimulatory activities (Krug et al., 2001. Identification of CpG oligonucleotide sequences with high induction of IFNalpha/beta in plasmacytoid dendritic cells. Eur J Immunol, 31(7): 2154-63; Marshall et al., 2005. Superior activity of the type C class of ISS in vitro and in vivo across multiple species. DNA Cell Biol. 24(2):63-72). Type A CpG ODNs are characterized by a phosphodiester central CpG-containing palindromic motif and a phosphorothioate 3' poly-G string. They induce high IFN-α production from plasmacytoid dendritic cells (pDC) but are weak stimulators of TLR9-dependent NF-kB signaling. Type B CpG ODNs contain a phosphorothioate backbone with one or more CpG dinucleotides. They strongly activate B cells but stimulate weakly IFN-α secretion. Type C CpG ODNs combine features of both types A and B. They contain a phosphorothioate backbone and a CpG-containing palindromic motif. Type C CpG ODNs induce strong IFN-α production from pDC and B cell stimulation.

Examples of non-limiting TLR9 ligand-enriched plasmids are described in Roman et al. (1997). Modifications of oligonucleotides include, but are not limited to, modifications of the 3'OH or 5'OH group, modifications of the nucleotide base, modifications of the sugar component, and modifications of the phosphate group.

A TLR9 ligand may comprise at least one nucleoside comprising an L-sugar. The L-sugar may be deoxyribose, ribose, pentose, deoxypentose, hexose, deoxyhexose, glucose, galactose, arabinose, xylose, lyxose, or a sugar "analog" cyclopentyl group. The L-sugar may be in pyranosyl or furanosyl form.

TLR9 ligands generally do not provide for, nor is there any requirement that they provide for, expression of any amino acid sequence encoded by the polynucleotide, and thus the sequence of a TLR9 ligand may be, and generally is, non-coding. TLR9 ligands may comprise a linear double or single-stranded molecule, a circular molecule, or can comprise both linear and circular segments. TLR9 ligands may be single-stranded, or may be completely or partially double-stranded.

In some embodiments, a TLR9 ligand for use in a subject method is an oligonucleotide, e.g., consists of a sequence of from about 5 nucleotides to about 200 nucleotides, from about 10 nucleotides to about 100 nucleotides, from about 12 nucleotides to about 50 nucleotides, from about 15 nucleotides to about 25 nucleotides, from 20 nucleotides to about 30 nucleotides, from about 5 nucleotides to about 15 nucleotides, from about 5 nucleotides to about 10 nucleotides, or from about 5 nucleotides to about 7 nucleotides in length. In some embodiments, a TLR9 ligand that is less than about 15 nucleotides, less than about 12 nucleotides, less than about 10 nucleotides, or less than about 8 nucleotides in length is associated with a larger molecule.

In some embodiments, a TLR9 ligand does not provide for expression of a peptide or polypeptide in a eukaryotic cell, e.g., introduction of a TLR9 ligand into a eukaryotic cell does not result in production of a peptide or polypeptide, because the TLR9 ligand does not provide for transcription of an mRNA encoding a peptide or polypeptide. In these embodiments, a TLR9 ligand lacks promoter regions and other control elements necessary for transcription in a eukaryotic cell.

A TLR9 ligand can be isolated from a bacterium, e.g., separated from a bacterial source; produced by synthetic methods (e.g., produced by standard methods for chemical synthesis of polynucleotides); produced by standard recombinant methods, then isolated from a bacterial source; or a combination of the foregoing. In many embodiments, a TLR9 ligand is purified, e.g., is at least about 80%, at least about 90%, at least about 95%, at least about 98%, at least about 99%, or more, e.g., 99.5%, 99.9%, or more, pure. In many embodiments, the TLR9 ligand is chemically synthesized, then purified.

In other embodiments, a TLR9 ligand is part of a larger nucleotide construct (e.g., a plasmid vector, a viral vector, or other such construct). A wide variety of plasmid and viral vector are known in the art, and need not be elaborated upon here. A large number of such vectors have been described in various publications, including, e.g., Current Protocols in Molecular Biology, (1987, and updates).

In general, a TLR9 ligand used in a subject composition comprises at least one unmethylated CpG motif. The relative position of any CpG sequence in a polynucleotide in certain mammalian species (e.g., rodents) is 5'-CG-3'(i.e., the C is in the 5' position with respect to the G in the 3' position).

In some embodiments, a TLR9 ligand comprises a central palindromic core sequence comprising at least one CpG sequence, where the central palindromic core sequence contains a phosphodiester backbone, and where the central palindromic core sequence is flanked on one or both sides by phosphorothioate backbone-containing polyguanosine sequences.

In other embodiments, a TLR9 ligand comprises one or more TCG sequences at or near the 5' end of the nucleic acid; and at least two additional CG dinucleotides. In some of these embodiments, the at least two additional CG dinucleotides are spaced three nucleotides, two nucleotides, or one nucleotide apart. In some of these embodiments, the at least two additional CG dinucleotides are contiguous with one another. In some of these embodiments, the TLR9 ligand comprises (TCG)n, where n=1 to 3, at the 5' end of the nucleic acid. In other embodiments, the TLR9 ligand comprises (TCG)n, where n=1 to 3, and where the (TCG)n sequence is flanked by one nucleotide, two nucleotides, three nucleotides, four nucleotides, or five nucleotides, on the 5' end of the (TCG)n sequence.

Exemplary consensus CpG motifs of TLR9 ligands useful herein include, but are not necessarily limited to: 5'-Purine-Purine-(C)-(G)-Pyrimidine-Pyrimidine-3', in which the TLR9 ligand comprises a CpG motif flanked by at least two purine nucleotides (e.g., GG, GA, AG, AA, II, etc.,) and at least two pyrimidine nucleotides (CC, TT, CT, TC, UU, etc.); 5'-Purine-TCG-Pyrimidine-Pyrimidine-3; 5'-TCG-N-N-3'; where N is any base; 5'-Nx(CG)nNy, where N is any base, where x and y are independently any integer from 0 to 200, e.g., 0, 1, 2, 3, 4, 5, 6, 7, 8, 9, 10, 11-15, 16-20, 21-25, 25-30, 30-50, 50-75, 75-100, 100-150, or 150-200; and n is any integer that is 1 or greater, e.g., 1, 2, 3, 4, 5, 6, 7, 8, 9, 10, or greater. 5'-Nx(TCG)nNy, where N is any base, where x and y are independently any integer from 0 to 200, e.g., 0, 1, 2, 3, 4, 5, 6, 7, 8, 9, 10, 11-15, 16-20, 21-25, 25-30, 30-50, 50-75, 75-100, 100-150, or 150-200; and n is any integer that is 1 or greater, e.g., 1, 2, 3, 4, 5, 6, 7, 8, 9, 10, or greater.

5'-(TCG)n-3', where n is any integer that is 1 or greater, e.g., to provide a TCG-based TLR9 ligand (e.g., where n=3, the polynucleotide comprises the sequence 5'-TCGNNTCGNNTCG-3'); 5'Nm-(TCG)n-Np-3', where N is any nucleotide, where m is zero, one, two, or three, where n is any integer that is 1 or greater, and where p is one, two, three, or four; 5'Nm-(TCG)n-Np-3', where N is any nucleotide, where m is zero to 5, and where n is any integer that is 1 or greater, where p is four or greater, and where the sequence N-N-N-N comprises at least two CG dinucleotides that are either contiguous with each other or are separated by one nucleotide, two nucleotides, or three nucleotides; and 5'-Purine-Purine-CG-Pyrimidine-TCG-3'.

Where a nucleic acid TLR9 ligand comprises a sequence of the formula: 5'-Nm-(TCG)n-Np-3', where N is any nucleotide, where m is zero to 5, and where n is any integer that is 1 or greater, where p is four or greater, and where the sequence N-N-N-N comprises at least two CG dinucleotides that are either contiguous with each other or are separated by one nucleotide, two nucleotides, or three nucleotides, exemplary TLR9 ligands that may be used include, but are not necessarily limited to: (1) a sequence of the formula in which n=2, and Np is NNCGNNCG; (2) a sequence of the formula in which n=2, and Np is AACGTTCG; (3) a sequence of the formula in which n=2, and Np is TTCGAACG; (4) a sequence of the formula in which n=2, and Np is TACGTACG; (5) a sequence of the formula in which n=2, and Np is ATCGATCG; (6) a sequence of the formula in which n=2, and Np is CGCGCGCG; (7) a sequence of the formula in which n=2, and Np is GCCGGCCG; (8) a sequence of the formula in which n=2, and Np is CCCGGGCG; (9) a sequence of the formula in which n=2, and Np is GGCGCCCG; (10) a sequence of the formula in which n=2, and Np is CCCGTTCG; (11) a sequence of the formula in which n=2, and Np is GGCGTTCG; (12) a sequence of the formula in which n=2, and Np is TTCGCCCG; (13) a sequence of the formula in which n=2, and Np is TTCGGGCG; (14) a sequence of the formula in which n=2, and Np is AACGCCCG; (15) a sequence of the formula in which n=2, and Np is AACGGGCG; (16) a sequence of the formula in which n=2, and Np is CCCGAACG; and (17) a sequence of the formula in which n=2, and Np is GGCGAACG; and where, in any of 1-17, m=zero, one, two, or three.

Where a nucleic acid TLR9 ligand comprises a sequence of the formula: 5'Nm-(TCG)n-Np-3', where N is any nucleotide, where m is zero, one, two, or three, where n is any integer that is 1 or greater, and where p is one, two, three, or four, exemplary TLR9 ligands that may be used include, but are not necessarily limited to: (1) a sequence of the formula where m=zero, n=1, and Np is T-T-T; (2) a sequence of the formula where m=zero, n=1, and Np is T-T-T-T; (3) a sequence of the formula where m=zero, n=1, and Np is C-C-C-C; (4) a sequence of the formula where m=zero, n=1, and Np is A-A-A-A; (5) a sequence of the formula where m=zero, n=1, and Np is A-G-A-T; (6) a sequence of the formula where Nm is T, n=1, and Np is T-T-T; (7) a sequence of the formula where Nm is A, n=1, and Np is T-T-T; (8) a sequence of the formula where Nm is C, n=1, and Np is T-T-T; (9) a sequence of the formula where Nm is G, n=1, and Np is T-T-T; (10) a sequence of the formula where Nm is T, n=1, and Np is A-T-T; (11) a sequence of the formula where Nm is A, n=1, and Np is A-T-T; and (12) a sequence of the formula where Nm is C, n=1, and Np is A-T-T.

The core structure of a TLR9 ligand may be flanked upstream and/or downstream by any number or composition of nucleotides or nucleosides. In some embodiments, the core sequence of a TLR9 ligand is at least 6 bases or 8 bases in length, and the complete TLR9 ligand (core sequences plus flanking sequences 5', 3' or both) is usually between 6 bases or 8 bases, and up to about 200 bases in length.

DNA-based TLR9 ligands include, but are not necessarily limited to, polynucleotides comprising one or more of the following nucleotide sequences:

AGCGCT, AGCGCC, AGCGTT, AGCGTC, AACGCT, AACGCC,

AACGTT, AACGTC, GGCGCT, GGCGCC, GGCGTT, GGCGTC,

GACGCT, GACGCC, GACGTT, GACGTC, GTCGTC, GTCGCT,

GTCGTT, GTCGCC, ATCGTC, ATCGCT, ATCGTT, ATCGCC,

TCGTCG,
and

TCGTCGTCG.

Additional TLR9 ligands include, but are not necessarily limited to, polynucleotides comprising one or more of the following nucleotide sequences:

TCGXXXX, TCGAXXX, XTCGXXX, XTCGAXX, TCGTCGA,

TCGACGT, TCGAACG, TCGAGAT, TCGACTC, TCGAGCG,

TCGATTT, TCGCTTT, TCGGTTT, TCGTTTT, TCGTCGT,

ATCGATT, TTCGTTT, TTCGATT, ACGTTCG, AACGTTC,

TGACGTT, TGTCGTT, TCGXXX, TCGAXX, TCGTCG, AACGTT,

ATCGAT, GTCGTT, GACGTT, TCGXX, TCGAX, TCGAT,

TCGTT, TCGTC, TCGA, TCGT, TCGX, and TCG (where "X"

is any nucleotide).

DNA-based TLR9 ligands include, but are not necessarily limited to, polynucleotides comprising the following octameric nucleotide sequences:

AGCGCTCG, AGCGCCCG, AGCGTTCG, AGCGTCCG, AACGCTCG,

AACGCCCG, AACGTTCG, AACGTCCG, GGCGCTCG, GGCGCCCG,

GGCGTTCG, GGCGTCCG, GACGCTCG, GACGCCCG, GACGTTCG,
and

GACGTCCG.

A TLR9 ligand can comprise one or more of any of the above CpG motifs. For example, a TLR9 ligand can comprise a single instance or multiple instances (e.g., 2, 3, 4, 5 or more) of the same CpG motif. Alternatively, a TLR9 ligand can comprise multiple CpG motifs (e.g., 2, 3, 4, 5 or more) where at least two of the multiple CpG motifs have different consensus sequences, or where all CpG motifs in the TLR9 ligand have different consensus sequences.

A TLR9 ligand may or may not include palindromic regions. If present, a palindrome may extend only to a CpG motif, if present, in the core hexamer or octamer sequence, or may encompass more of the hexamer or octamer sequence as well as flanking nucleotide sequences.

In certain aspects the TLR9 agonists can be an TLR9 oligonucleotide agonist, including but not limited to type A CpG oligodeoxynucleotide, a type B CpG oligodeoxynucleotide, a type C CpG oligodeoxynucleotides or other oligodeoxynucleotides. In certain aspects the TLR9 agonist is a type C oligodeoxynucleotide (ODN), such as ODN2395 (5'-tcgtcgttttcggcgcgcgccg-3' (22 mer)SEQ ID NO:) or ODNM362 (5'-tcgtcgtcgttcgaacgacgttgat-3' (25 mer) SEQ ID NO:) or ODN10101 (5'-tcgtcgttttcgcgcgcgccg-3' SEQ ID NO:) or 9 mer (5'-cgcgaagcg-3' SEQ ID NO:) or H-Tel 22 (5'-agggttagggttagggttaggg-3' SEQ ID NO:) or analog thereof. In particular aspects the TLR9 oligonucleotide has a phosphorothioate or phosphodiester backbone.

Multimeric TLR9 Ligands.

In some embodiments, a TLR9 ligand is multimeric. A multimeric TLR9 ligand comprises two, three, four, five, six, seven, eight, nine, ten, or more individual (monomeric) nucleic acid TLR9 ligands, as described above, linked via non-covalent bonds, linked via covalent bonds, and either linked directly to one another, or linked via one or more spacers. Suitable spacers include nucleic acid and non-nucleic acid molecules, as long as they are biocompatible. In some embodiments, multimeric TLR9 ligand comprises a linear array of monomeric TLR9 ligands. In other embodiments, a multimeric TLR9 ligand is a branched, or dendrimeric, array of monomeric TLR9 ligands.

In some embodiments, a multimeric TLR9 ligand has the general structure (X1)n(X2)n where X is a nucleic acid TLR9 ligand as described above, and having a length of from about 6 nucleotides to about 200 nucleotides, e.g., from about 6 nucleotides to about 8 nucleotides, from about 8 nucleotides to about 10 nucleotides, from about 10 nucleotides to about 12 nucleotides, from about 12 nucleotides to about 15 nucleotides, from about 15 nucleotides to about 20 nucleotides, from about 20 nucleotides to about 25 nucleotides, from about 25 nucleotides to about 30 nucleotides, from about 30 nucleotides to about 40 nucleotides, from about 40 nucleotides to about 50 nucleotides, from about 50 nucleotides to about 60 nucleotides, from about 60 nucleotides to about 70 nucleotides, from about 70 nucleotides to about 80 nucleotides, from about 80 nucleotides to about 90 nucleotides, from about 90 nucleotides to about 100 nucleotides, from about 100 nucleotides to about 125 nucleotides, from about 125 nucleotides to about 150 nucleotides, from about 150 nucleotides to about 175 nucleotides, or from about 175 nucleotides to about 200 nucleotides; and where n is any number from one to about 100, e.g., n=1, 2, 3, 4, 5, 6, 7, 8, 9, 10, from 10 to about 15, from 15 to about 20, from 20 to about 25, from 25 to about 30, from 30 to about 40, from 40 to about 50, from 50 to about 60, from 60 to about 70, from 70 to about 80, from 80 to about 90, or from 90 to about 100. In these embodiments, X and X2 differ in nucleotide sequence from one another by at least one nucleotide, and may differ in nucleotide sequence from one another by two, three, four, five, six, seven, eight, nine, ten, or more bases.

As noted above, in some embodiments, a subject multimeric TLR9 ligand comprises a TLR9 ligand separated from an adjacent TLR9 ligand by a spacer. In some embodiments, a spacer is a non-TLR9 ligand nucleic acid. In other embodiments, a spacer is a non-nucleic acid moiety. Suitable spacers include those described in U.S. Patent Publication 20030225016. A TLR9 ligand is multimerized using any known method.

TLR9 Ligand Modifications.

A TLR9 ligand suitable for use in a subject composition can be modified in a variety of ways. For example, a TLR9 ligand can comprise backbone phosphate group modifications (e.g., methylphosphonate, phosphorothioate, phosphoroamidate and phosphorodithioate internucleotide linkages), which modifications can, for example, enhance their stability in vivo, making them particularly useful in therapeutic applications. A particularly useful phosphate group modification is the conversion to the phosphorothioate or phosphorodithioate forms of a nucleic acid TLR9 ligand. Phosphorothioates and phosphorodithioates are more resistant to degradation in vivo than their unmodified oligonucleotide counterparts, increasing the half-lives of the TLR9 ligands and making them more available to the subject being treated.

Other modified TLR9 ligands include TLR9 ligands having modifications at the 5' end, the 3' end, or both the 5' and 3' ends. For example, the 5' and/or 3' end can be covalently or non-covalently associated with a molecule (either nucleic acid, non-nucleic acid, or both) to, for example, increase the bio-availability of the TLR9 ligand, increase the efficiency of uptake where desirable, facilitate delivery to cells of interest, and the like. Molecules for conjugation to a TLR9 ligand include, but are not necessarily limited to, cholesterol, phospholipids, fatty acids, sterols, oligosaccharides, polypeptides (e.g., immunoglobulins), peptides, antigens (e.g., peptides, small molecules, etc.), linear or circular nucleic acid molecules (e.g., a plasmid), insoluble supports, therapeutic polypeptides, and the like. Therapeutic polypeptides that are suitable for attachment to a TLR9 agonist include, but are not limited to, a dendritic cell growth factor (e.g., GM-CSF); a cytokine; an interferon (e.g., an IFN-α, an IFN-β, etc.); a TNF-α antagonist; and the like.

A TLR9 ligand is in some embodiments linked (e.g., conjugated, covalently linked, non-covalently associated with, or adsorbed onto) an insoluble support. An exemplary, non-limiting example of an insoluble support is cationic poly(D,L-lactide-co-glycolide).

Additional TLR9 ligand conjugates, and methods for making same, are known in the art and described in, for example, WO 98/16427 and WO 98/55495. Thus, the term TLR9 ligand" includes conjugates comprising a nucleic acid TLR9 ligand.

A polypeptide, e.g., a therapeutic polypeptide, may be conjugated directly or indirectly, e.g., via a linker molecule, to a TLR9 ligand. A wide variety of linker molecules are known in the art and can be used in the conjugates. The linkage from the peptide to the oligonucleotide may be through a peptide reactive side chain, or the N- or C-terminus of the peptide. Linkage from the oligonucleotide to the peptide may be at either the 3' or 5' terminus, or internal. A linker may be an organic, inorganic, or semi-organic molecule, and may be a polymer of an organic molecule, an inorganic molecule, or a co-polymer comprising both inorganic and organic molecules.

If present, the linker molecules are generally of sufficient length to permit oligonucleotides and/or polynucleotides and a linked polypeptide to allow some flexible movement between the oligonucleotide and the polypeptide. The linker molecules are generally about 6-50 atoms long. The linker molecules may also be, for example, aryl acetylene, ethylene glycol oligomers containing 2-10 monomer units, diamines, diacids, amino acids, or combinations thereof. Other linker molecules which can bind to oligonucleotides may be used in light of this disclosure.

III. FORMULATIONS AND ADMINISTRATION

The inventors have used the mouse as a model for studying the stimulation by compositions described herein. The effects of single and repetitive exposure of a subject to a composition described herein have been determined and no obvious gross pathology, such as premature death, weight loss, or behavioral changes have been observed.

One non-limiting benefit of embodiments described herein is that it can be delivered and have effect quickly and easily. Also, the compositions can be produced economically in large quantities and easily stored, as well as easily transported by a person outside of a hospital setting.

The pharmaceutical compositions disclosed herein may be administered via the respiratory system of a subject. In certain aspects the compositions are deposited in the lung by methods and devices known in the art. Compositions may be prepared in water suitably mixed with a surfactant, such as hydroxypropylcellulose. Dispersions may also be prepared in glycerol, liquid polyethylene glycols and mixtures thereof, and in oils. Under ordinary conditions of storage and use, these preparations contain a preservative to prevent the growth of microorganisms. The pharmaceutical forms suitable for inhalation include sterile aqueous solutions or dispersions and sterile powders for the extemporaneous preparation of sterile inhalable solutions or dispersions. In all cases the form is typically sterile and capable of inhalation directly or through some intermediary process or device. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. The prevention of the action of microorganisms can be brought about by various antibacterial and antifungal agents, for example, parabens, chlorobutanol, phenol, sorbic acid, thimerosal, and the like.

Some variation in dosage will necessarily occur depending on the condition of the subject being treated and the particular circumstances involving exposure or potential exposure. The person responsible for administration will, in any event, determine the appropriate dose for the individual subject. Moreover, for human administration, preparations should meet sterility, pyrogenicity, general safety, and purity standards as required by FDA Office of Biologics standards or other similar organizations.

Sterile compositions are prepared by incorporating the active components in the required amount in the appropriate solvent with various other ingredients enumerated above, as required, followed by, for example, filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile compositions, some methods of preparation are vacuum-drying and freeze-drying techniques which yield a powder of the active ingredient plus any additional desired ingredient from a previously sterile-filtered solution.

Pulmonary/respiratory drug delivery can be implemented by different approaches, including liquid nebulizers, aerosol-based metered dose inhalers (MDI's), sprayers, dry powder dispersion devices and the like. Such methods and compositions are well known to those of skill in the art, as indicated by U.S. Pat. Nos. 6,797,258, 6,794,357, 6,737,045, and 6,488,953, all of which are incorporated by reference. According to some embodiments, at least one pharmaceutical composition can be delivered by any of a variety of inhalation or nasal devices known in the art for administration of a therapeutic agent by inhalation. Other devices suitable for directing pulmonary or nasal administration are also known in the art. Typically, for pulmonary administration, at least one pharmaceutical composition is delivered in a particle size effective for reaching the lower airways of the lung or sinuses. Some specific examples of commercially available inhalation devices suitable for the practice of methods are Turbohaler™ (Astra), Rotahaler® (Glaxo), Diskus® (Glaxo), Spiros™ inhaler (Dura), devices marketed by Inhale Therapeutics, AERx™ (Aradigm), the Ultravent® nebulizer (Mallinckrodt), the Acorn II® nebulizer (Marquest Medical Products), the Ventolin® metered dose inhaler (Glaxo), the Spinhaler® powder inhaler (Fisons), or the like.

All such inhalation devices can be used for the administration of a pharmaceutical composition in an aerosol. Such aerosols may comprise either solutions (both aqueous and non aqueous) or solid particles. Metered dose inhalers typically use a propellant gas and require actuation during inspiration. See, e.g., WO 98/35888; WO 94/16970. Dry powder inhalers use breath-actuation of a mixed powder. See U.S. Pat. Nos. 5,458,135; 4,668,218; PCT publications WO 97/25086; WO 94/08552; WO 94/06498; and European application EP 0237507, each of which is incorporated herein by reference in their entirety. Nebulizers produce aerosols from solutions, while metered dose inhalers, dry powder inhalers, and the like generate small particle aerosols. Suitable formulations for administration include, but are not limited to nasal spray or nasal drops, and may include aqueous or oily solutions of a StIR composition.

A spray comprising a pharmaceutical composition can be produced by forcing a suspension or solution of a composition through a nozzle under pressure. The nozzle size and configuration, the applied pressure, and the liquid feed rate can be chosen to achieve the desired output and particle size. An electrospray can be produced, for example, by an electric field in connection with a capillary or nozzle feed.

A pharmaceutical composition can be administered by a nebulizer such as a jet nebulizer or an ultrasonic nebulizer. Typically, in a jet nebulizer, a compressed air source is used to create a high-velocity air jet through an orifice. As the gas expands beyond the nozzle, a low-pressure region is created, which draws a composition through a capillary tube connected to a liquid reservoir. The liquid stream from the capillary tube is sheared into unstable filaments and droplets as it exits the tube, creating the aerosol. A range of configurations, flow rates, and baffle types can be employed to achieve the desired performance characteristics from a given jet nebulizer. In an ultrasonic nebulizer, high-frequency electrical energy is used to create vibrational, mechanical energy, typically employing a piezoelectric transducer. This energy is transmitted to the composition creating an aerosol.

In a metered dose inhaler (MDI), a propellant, a composition, and any excipients or other additives are contained in a canister as a mixture with a compressed gas. Actuation of the metering valve releases the mixture as an aerosol.

Pharmaceutical compositions for use with a metered-dose inhaler device will generally include a finely divided powder containing a composition described herein as a suspension in a non-aqueous medium, for example, suspended in a propellant with the aid of a surfactant. The propellant can be any conventional material employed for this purpose such as chlorofluorocarbon, a hydrochlorofluorocarbon, a hydrofluorocarbon, or a hydrocarbon including trichlorofluoromethane, dichlorodifluoromethane, dichlorotetrafluoroethanol and 1,1,1,2-tetrafluoroethane, HFA-134a (hydrofluroalkane-134a), HFA-227 (hydrofluroalkane-227), or the like.

Methods may involve administering to the patient or subject at least or at most 1, 2, 3, 4, 5, 6, 7, 8, 9, 10 or more doses of a therapeutic composition. A dose may be a composition comprising about, at least about, or at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7. 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0. 19.5, 20.0, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 6000, 7000, 8000, 9000, 10000 milligrams (mg) or micrograms (mcg) or µg/ml or micrograms/ml or mM or µM (or any range derivable therein) of each TLR agonist or total amount of a combination of TLR agonists, or an antigen or allergen.

A dose may be administered on an as needed basis or every 1, 2, 3, 4, 5, 6, 7, 8, 9, 10, 11, 12, 18, or 24 hours (or any range derivable therein) or 1, 2, 3, 4, 5, 6, 7, 8, 9, or times per day (or any range derivable therein). A dose may be first administered before or after signs of an infection are exhibited or felt by a patient or after a clinician evaluates the patient for an infection. In some embodiments, the patient is administered a first dose of a regimen 1, 2, 3, 4, 5, 6, 7, 8, 9, 10, 11, 12 hours (or any range derivable therein) or 1, 2, 3, 4, or 5 days after the patient experiences or exhibits signs or symptoms of an infection (or any range derivable therein). The patient may be treated for 1, 2, 3, 4, 5, 6, 7, 8, 9, 10 or more days (or any range derivable therein) or until symptoms of an infection have disappeared or been reduced or after 6, 12, 18, or 24 hours or 1, 2, 3, 4, or 5 days after symptoms of an infection have disappeared or been reduced.

In compositions comprising two TLR agonists, the ratio of the two TLR agonists may be about 1:1, 2:1, 3:1, 4:1, 5:1, 6:1, 7:1, 8:1, 9:1, 10:1, 11:1, 12:1, 13:1, 14:1, 15:1, 20:1, 30; 1, 40:1, 50:1, 60:1, 70:1, 80:1, 90:1, 100:1 or more, or any range derivable therein. In specific embodiments, the TLR agonists are TLR2/6 and TLR9 agonists (or vice versa).

Treatment with a nebulizer may be at least or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, or 120 minutes in length (or any range derivable therein). The nebulizer reservoir may contain a solution that comprises about, at least about or at most about 0.1, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430. 440. 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 µg/ml or mg/ml (or any range derivable therein) of each TLR agonist or the total amount of a combination of TLR agonists.

The volume that is administered in each dose may be about, at least about, or at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7. 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0. 19.5, 20.0, 1, 2, 3, 4, 5, 6, 7, 8, 9, 10, 11, 12, 13, 14, 15, 16, 17, 18, 19, 20 µl or ml (or any range derivable therein).

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically acceptable" refers to molecular entities and compositions that do not produce an allergic or similar untoward reaction when administered to a subject. The preparation of an aqueous composition that contains a polypeptide or peptide as an active ingredient is well understood in the art.

Compositions and methods may be used in the context of a number of therapeutic or prophylactic applications. In order to increase the effectiveness of a treatment with the compositions described herein or to augment the protection of another therapy (second therapy), e.g., anti-allergy therapy. Alternatively, it is contemplated that the therapy involving TLR agonists is contemplated for use after the subject has tried traditional therapy with little or limited success. Administration of a composition to a subject will follow general protocols for the administration via the respiratory system, and the general protocols for the administration of a particular secondary therapy will also be followed, taking into account the toxicity, if any, of the treatment. It is expected that the treatment cycles would be repeated as necessary. It also is contemplated that various standard therapies, as well as vaccination, may be applied in combination with the described therapies.

In certain aspects an anti-inflammatory agent may be used in combination with a TLR or O/P composition. In particular embodiments, a patient is treated with an asthma therapeutic, such as one or more fast acting medicines to treat acute symptoms and/or a long term control medicine. Examples of fast acting medicines include but are not limited to beta2-adrenoceptor agonists (SABA), such as salbutamol or albuterol, anticholinergic medications such as ipratropium bromide, and adrenergic agonists such as epinephrine. Examples of long term control medications include, but are not limited to, glucocorticoids, long acting beta adrenoceptor agonists (LABA), leukotriene antagonists, or mast cell stabilizers.

Steroidal anti-inflammatories for use herein include, but are not limited to fluticasone, beclomethasone, any pharmaceutically acceptable derivative thereof, and any combination thereof. As used herein, a pharmaceutically acceptable derivative includes any salt, ester, enol ether, enol ester, acid, base, solvate or hydrate thereof. Such derivatives may be prepared by those of skill in the art using known methods for such derivatization.

Fluticasone—

Fluticasone propionate is a synthetic corticosteroid and has the empirical formula $C_{25}H_{31}F_3O_5S$. It has the chemical name S-(fluromethyl)6α,9-difluoro-11β-17-dihydroxy-16α-methyl-3-oxoandrosta-1,4-diene-17β-carbothioate,17-propionate. Fluticasone propionate is a white to off-white powder with a molecular weight of 500.6 and is practically insoluble in water, freely soluble in dimethyl sulfoxide and dimethylformamide, and slightly soluble in methanol and 95% ethanol.

In an embodiment, formulations may comprise a steroidal anti-inflammatory (e.g., fluticasone propionate)

Beclomethasone—

In certain aspects the steroidal anti-inflammatory can be beclomethasone dipropionate or its monohydrate. Beclomethasone dipropionate has the chemical name 9-chloro-11b,17,21-trihydroxy-16b-methylpregna-1,4-diene-3,20-doine17,21-dipropionate. The compound may be a white powder with a molecular weight of 521.25; and is very slightly soluble in water (Physicians' Desk Reference), very soluble in chloroform, and freely soluble in acetone and in alcohol.

Providing steroidal anti-inflammatories may enhance the compositions and methods by, for example, attenuating any unwanted inflammation. Examples of other steroidal anti-inflammatories for use herein include, but are not limited to, betamethasone, triamcinolone, dexamethasone, prednisone, mometasone, flunisolide and budesonide.

In accordance with yet another embodiments, the non-steroidal anti-inflammatory agent may include aspirin, sodium salicylate, acetaminophen, phenacetin, ibuprofen, ketoprofen, indomethacin, flurbiprofen, diclofenac, naproxen, piroxicam, tebufelone, etodolac, nabumetone, tenidap, alcofenac, antipyrine, amimopyrine, dipyrone, animopyrone, phenylbutazone, clofezone, oxyphenbutazone, prexazone, apazone, benzydamine, bucolome, cinchopen, clonixin, ditrazol, epirizole, fenoprofen, floctafeninl, flufenamic acid, glaphenine, indoprofen, meclofenamic acid, mefenamic acid, niflumic acid, salidifamides, sulindac, suprofen, tolmetin, nabumetone, tiaramide, proquazone, bufexamac, flumizole, tinoridine, timegadine, dapsone, diflunisal, benorylate, fosfosal, fenclofenac, etodolac, fentiazac, tilomisole, carprofen, fenbufen, oxaprozin, tiaprofenic acid, pirprofen, feprazone, piroxicam, sudoxicam, isoxicam, celecoxib, Vioxx®, and/or tenoxicam.

Suitable pharmaceutically acceptable excipients may be volatile or nonvolatile. Volatile excipients, when heated, are concurrently volatilized, aerosolized and inhaled. Classes of such excipients are known in the art and include, without limitation, gaseous, supercritical fluid, liquid and solid solvents. The following is a list of exemplary carriers within these classes: water; terpenes, such as menthol; alcohols, such as ethanol, propylene glycol, glycerol and other similar alcohols; dimethylformamide; dimethylacetamide; wax; supercritical carbon dioxide; dry ice; and mixtures thereof. In certain aspects glycerol is utilized as an excipient.

IV. KITS

Any of the compositions described herein may be comprised in a kit. In a non-limiting example, reagents for production and/or delivery of a TLR or O/P composition are included in a kit. In certain aspects the kit is portable and may be carried on a person much like an asthma inhaler is carried.

The components of the kits may be packaged either in an aqueous, powdered, or lyophilized form. The container means of the kits will generally include at least one inhaler, canister, vial, test tube, flask, bottle, syringe or other container means, into which a component may be placed, and preferably, suitably aliquoted. Where there is more than one component in the kit (second agent, etc.), the kit also will generally contain a second, third or other additional container into which the additional components may be separately placed. However, various combinations of components may be comprised in a vial, canister, or inhaler. A container can include a canister or inhaler that can be worn on a belt or easily carried in a pocket, backpack or other storage container. Kits also may include a container for the described compositions or their variations, and any other reagent containers in close confinement for commercial sale. Such containers may include injection or blow molded plastic containers into which the desired vials are retained.

When the components of the kit are provided in one and/or more liquid solutions, e.g., the liquid solution is an aqueous solution, with a sterile aqueous solution being particularly preferred, but not required. However, the components of the kit may be provided as dried powder(s). When reagents and/or components are provided as a dry powder, the powder may be reconstituted by the addition of a suitable solvent or administered in a powdered form. It is envisioned that a solvent may also be provided in another container means.

A kit will also include instructions for employing the kit components as well the use of any other reagent not included in the kit. Instructions may include variations that can be implemented.

It is contemplated that such reagents are embodiments of kits. Such kits, however, are not limited to the particular items identified above and may include any reagent used directly or indirectly in the detection of pathogenic microorganisms or administration of a StIR composition.

V. EXAMPLES

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Activation of Lung Innate Immunity to Modulate the Asthmatic Immune Response

In this study, the inventors investigated a possible role for inducible innate resistance in the modulation of the asthmatic immune response using an experimental asthma mouse model. Analysis of serum immunoglobulins and differential cell counts of bronchoalveolar lavage (BAL) fluid revealed that aerosol administration of O/P with OVA significantly reduced OVA-specific IgE levels, as well as eosinophils in the BAL. Conversely, the inventors observed an increase in serum IgG2a levels, a marker of Th1 immunity. Together our findings suggest that activation of lung innate immunity with O/P combined with specific antigen can switch the allergic immune response to a non-allergic one.

A. Results

Aerosolized OVA-O/P Reduces Total- and OVA-IgE Serum Levels.

Figure 1B:
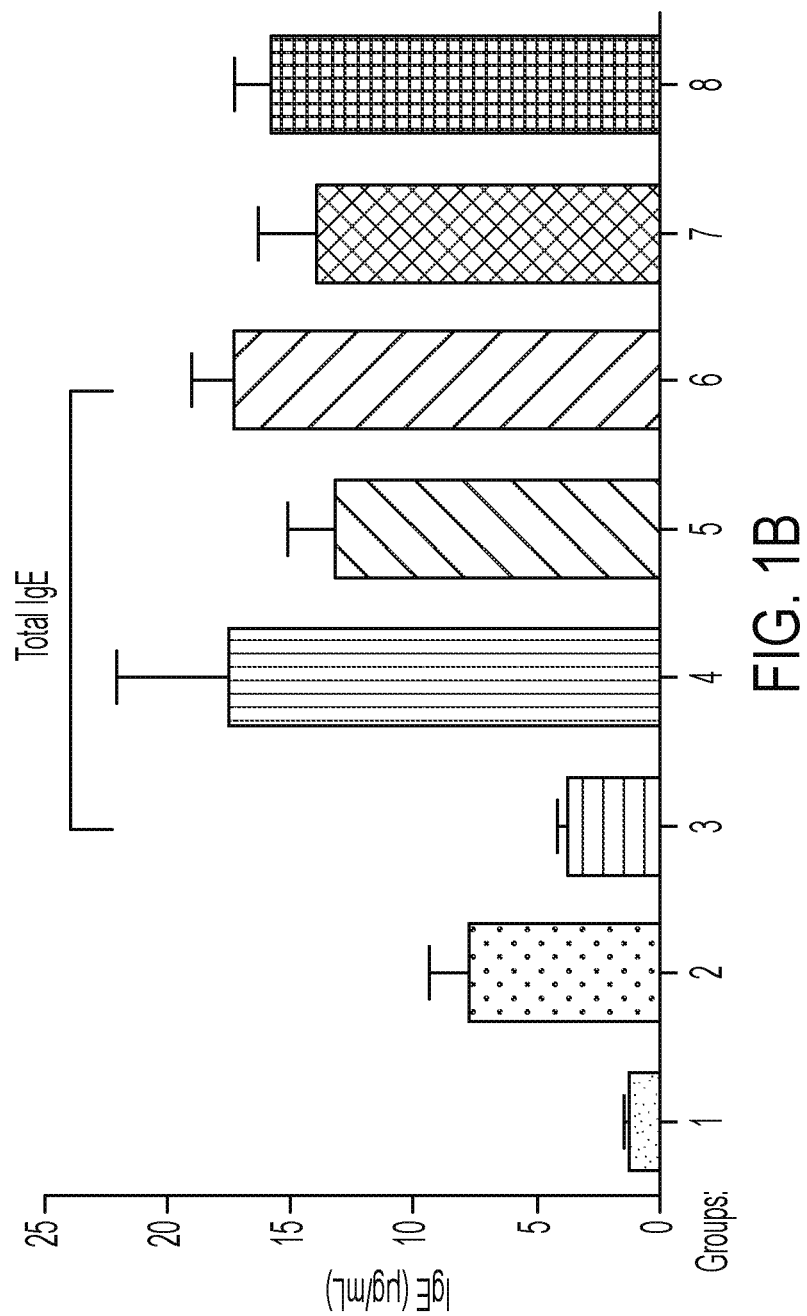

Preliminary studies with aerosolized O/P have demonstrated a powerful defensive response of the airway epithelium that can prevent respiratory infections caused by various viruses (Evans et al., Annu Rev Physiol (2010), 72:413-35; Clement et al., Am J Respir Crit Care Med (2008), 177:1322-30; Evans et al., Am J Respir Cell Mol Biol (2010), 42:40-50; Tuvim et al., PLoS ONE (2009) 4:e4176). To assess possible beneficial or harmful effects of O/P on allergic asthma, the inventors used a conventional mouse (BALB/c) ovalbumin sensitization and challenge model (FIG. 1A). The inventors assessed atopy, the allergic phenotype, by measuring serum IgE. Examination of total IgE levels in mice immunized and challenged with aerosolized OVA+/−O/P revealed a marked increase between aerosol-challenged mice (FIG. 1B, groups 4-8) and those that were immunized only (FIG. 1B, groups 2-3). However, although the inventors did not observe a significant change between mice immunized and challenged with OVA alone versus OVA-O/P (6×) (Groups 4 vs 6), a significant decrease in total IgE was observed in mice that were aerosol challenged 9× with OVA-O/P (FIG. 1B, Group 3 vs Group 6).

Figure 1C:
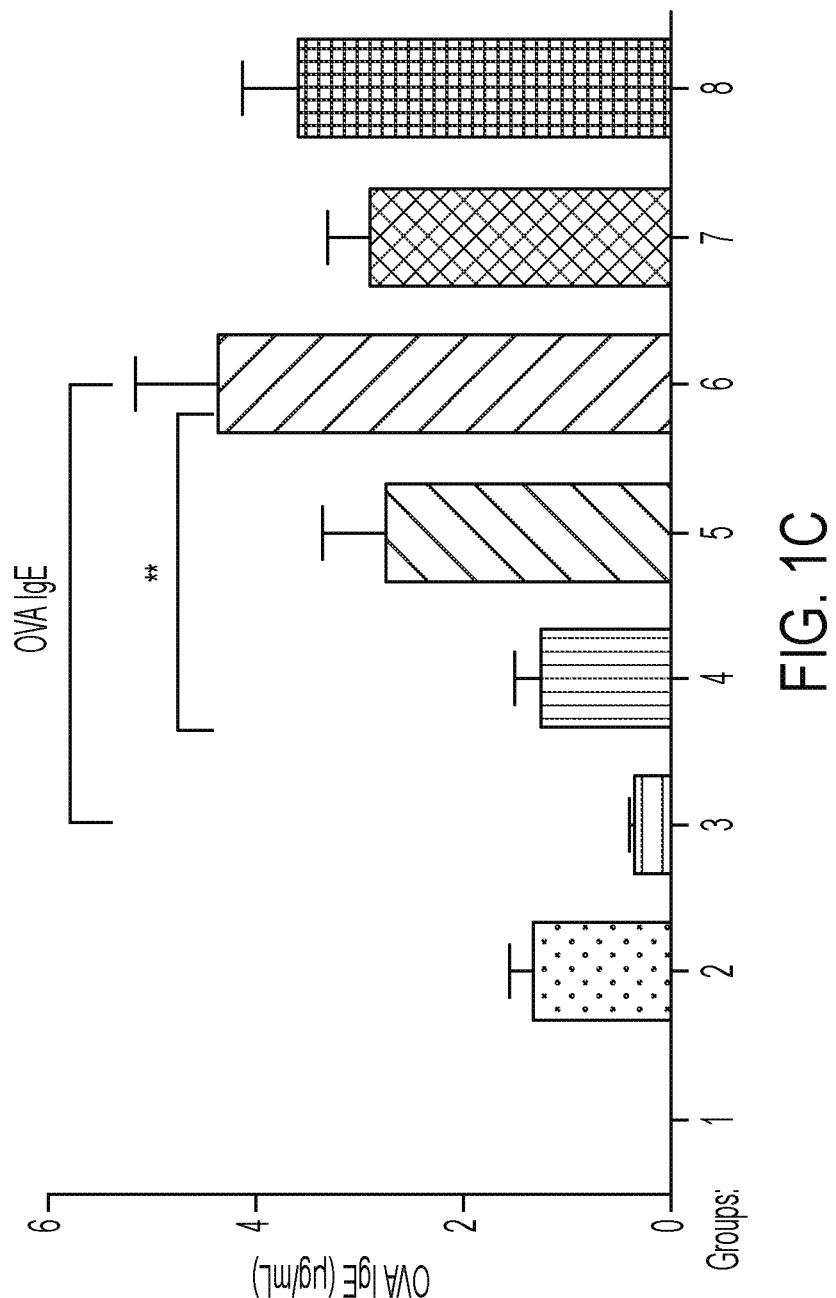

Measurement of OVA-specific IgE in serum also showed a robust increase in this allergic isotype between groups that were aerosol challenged with OVA (FIG. 1C, groups 4-8) and those that were immunized only (FIG. 1C, groups 2-3). However, this time a dramatic reduction in OVA-specific IgE was observed in mice aerosol challenged with OVA-O/P (6×) (FIG. 1C, Group 4, 1.26±0.26) as compared to OVA alone that was statistically significant (FIG. 1C, Group 6, asterisks, 4.36±0.82, P=0.005). Furthermore, there was an even greater reduction in OVA-IgE when mice were challenged 9× with aerosolized OVA-O/P as compared to OVA alone (FIG. 1C, Group 6: 4.36±0.82 vs. Group 3: 0.35±0.7, P=0.0008).

This result indicates that aerosol delivery of an antigen (OVA) combined with O/P leads to the reduction of both total and antigen specific IgE, the allergic immunoglobulin. Of note, there was a weak adjuvant effect of O/P given together with ovalbumin by aerosol that requires further study (FIGS. 1B and 1C, Group 5).

Aerosolized OVA-O/P Increases Serum IgG2a and IgG1 Levels.

Figure 2:
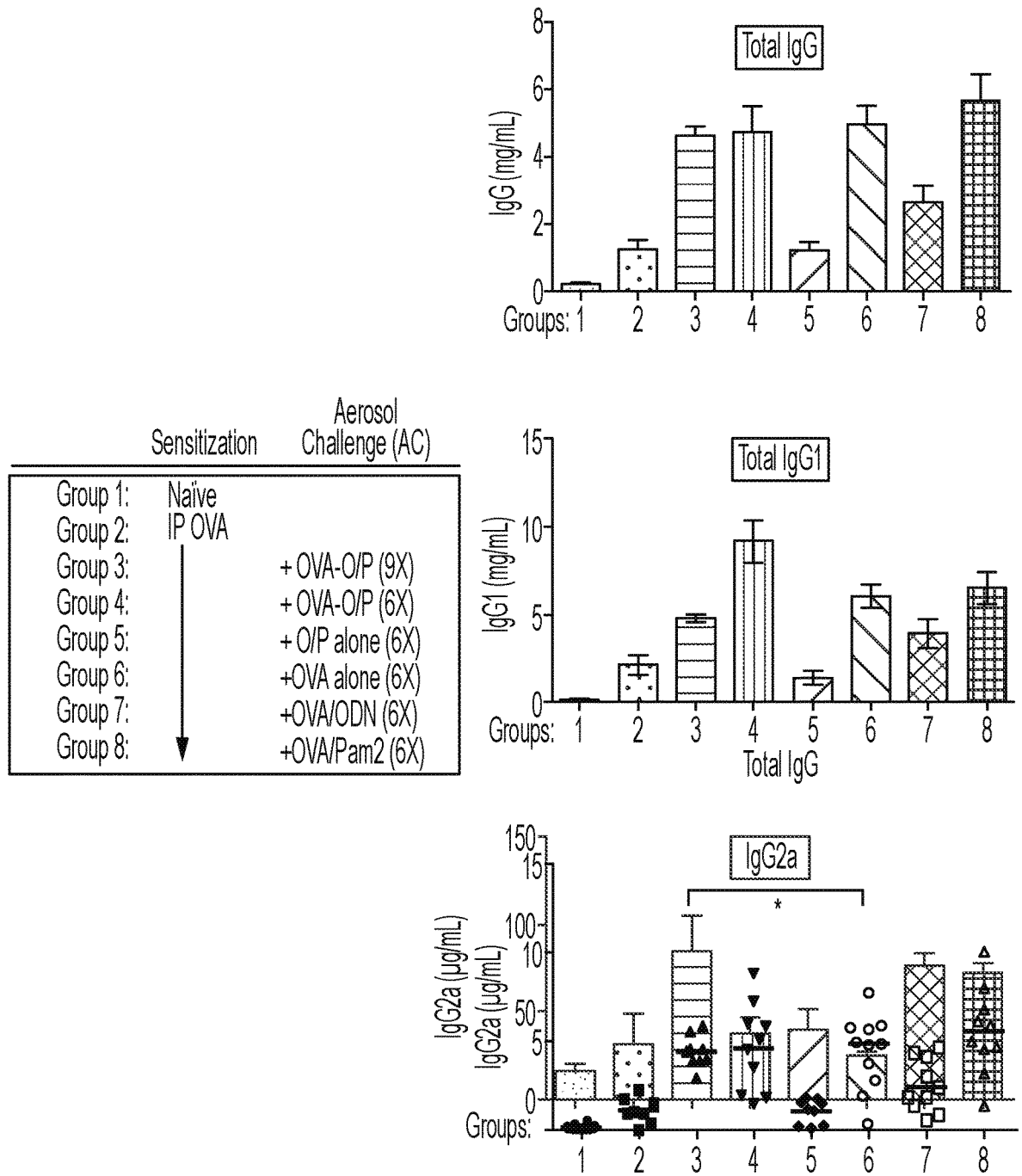
FIG. 2. Aerosolized O/P combined with OVA increases IgG2a, the Th1 marker and the anti-inflammatory IgG1 biomarker. BALB/c mice (n=10) were immunized as described in FIG. 1A (left panel). Sandwich ELISAs were used to measure total IgG, total IgG1, and total IgG2a levels from mouse serum samples as described in Materials and Methods. Comparison of mice treated with OVA alone (top panel, Group 6) with mice treated with OVA-O/P (top panel) did not reveal a significant difference in total IgG between the two groups. However, ELISAs for IgG1 did reveal a slight increase in IgG1 levels in OVA-O/P treated mice (Group 4, n=10, 9.16±1.18) as compared to OVA alone (Group 6, 6.01±0.66, P=0.035). In addition, ELISAs for IgG2a revealed a slight increase in IgG2a levels in OVA-O/P treated mice (Group 3, 8.4±21) as compared to OVA alone (Group 6, 25±3, P=0.02).

Next, the inventors assessed the IgG immunoglobulin subclasses to determine whether the OVA-O/P aerosol challenge model modulated the immune response by measuring total IgG, IgG1, and IgG2a serum levels (FIG. 2). All mice immunized and aerosol challenged with OVA showed increased serum levels of total IgG (FIG. 2, top panel, groups 3-4, 6-8), whereas mice given O/P (PUL-042) alone by aerosol did not (FIG. 2, top panel, group 5). Increased total IgG levels reflects a successful immunization protocol. Moreover, comparison of mice treated with OVA alone (top panel, Group 6) with mice treated with OVA-O/P (top panel) did not reveal a significant difference in total IgG between the two groups (FIG. 2, top panel, group 4 vs group 6).

In contrast, measurement of IgG1 did reveal a slight increase in IgG1 levels in OVA-O/P treated mice (Group 4, n=10, 9.16±1.18) as compared to OVA alone (Group 6, 6.01±0.66, P=0.035). Furthermore, measurement of IgG2a revealed a slight increase in IgG2a levels in OVA-O/P treated mice (Group 3, 8.4±21) as compared to OVA alone (Group 6, 25±3, P=0.02).

In humans, measurement of serum IgG4 levels (IgG1 in mice) has been used as a biomarker for successful immunotherapy (James et al., *J Allergy Clin Immunol* (2011), 127:509-16; Karsten et al., *Nat Med* (2012), 18:1401-06), and serum IgG2a levels in mice is commonly used as a biomarker for Th1 immunity. Together with total- and OVA-IgE results (FIG. 1), the data indicate that these mice switched their allergic response (IgE) to a non-allergic one (IgG2a and IgG1).

Optimization of OVA Allergic Sensitization Model.

A conventional allergic sensitization model is used routinely for studying allergic inflammation. However, it was unclear whether this sensitization/challenge protocol was optimal for immunomodulation studies with aerosolized O/P. To define an optimal temporal and quantitative allergic sensitization model a study was designed to determine the minimum number of OVA aerosol challenges required to generate a robust allergic response (FIG. 3A). Mice were given either one (Group 2, 4-6) or two (Group 3, 7-9) IP injections one week apart with OVA/alum followed by various OVA aerosol challenges starting on Day 7 as shown in FIG. 3A (top panel).

Figure 4:
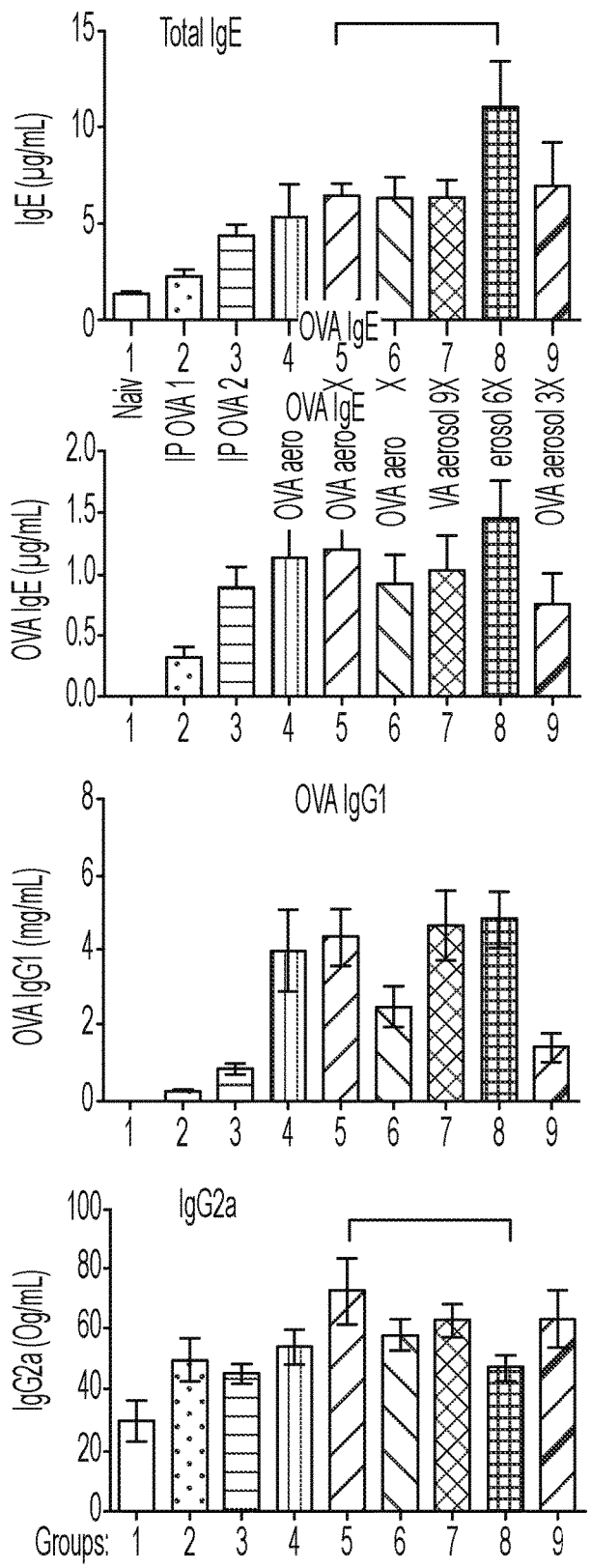
FIG. 4. Optimization of allergic sensitization measured by serum immunoglobulins. Balb/c mice (n=10) were immunized as described in FIG. 3A. Sandwich ELISAs were used to measure total IgE, OVA IgE, OVA IgG1, and IgG2a levels from mouse serum samples. Note that total IgE levels in Group 8 (upper panel, 11.05±2.39) are higher than Group 5 in this experiment (5.36±1.70, P=0.09) although not statistically significant.

Analysis of total cell counts from BAL revealed that mice in Groups 8 and 9 had the highest total leukocyte count as compared to other groups (FIG. 3B). In addition, this same group had the highest total eosinophil (EOS) count as compared to the other groups (FIG. 3B). Examination of total IgE, OVA IgE, OVA IgG1, and IgG2a serum levels by ELISA similarly revealed that total IgE levels in Group 8 (FIG. 4, upper panel, 11.05±2.39) were correspondingly higher than Group 5 (FIG. 4, upper panel, 5.36±1.70, P=0.09), although not statistically significant. Lastly, a trend was observed with IgG2a showing decreased serum levels in mice from Group 8, which correlates accurately with a robust allergic response (IgE) and a suppressed Th1 immune response (FIG. 4, bottom panel). There were no apparent differences in OVA-IgG1 serum levels in this sensitization model (FIG. 4, third panel).

In sum, the inventors defined an optimal allergic sensitization model for intervention with O/P requiring 2 OVA IP injections, one week apart, followed by 2 weekly OVA aerosol challenges for 3 weeks.

Determination of Most Efficacious Intervention with Aerosolized OVA-O/P.

Figure 5A:
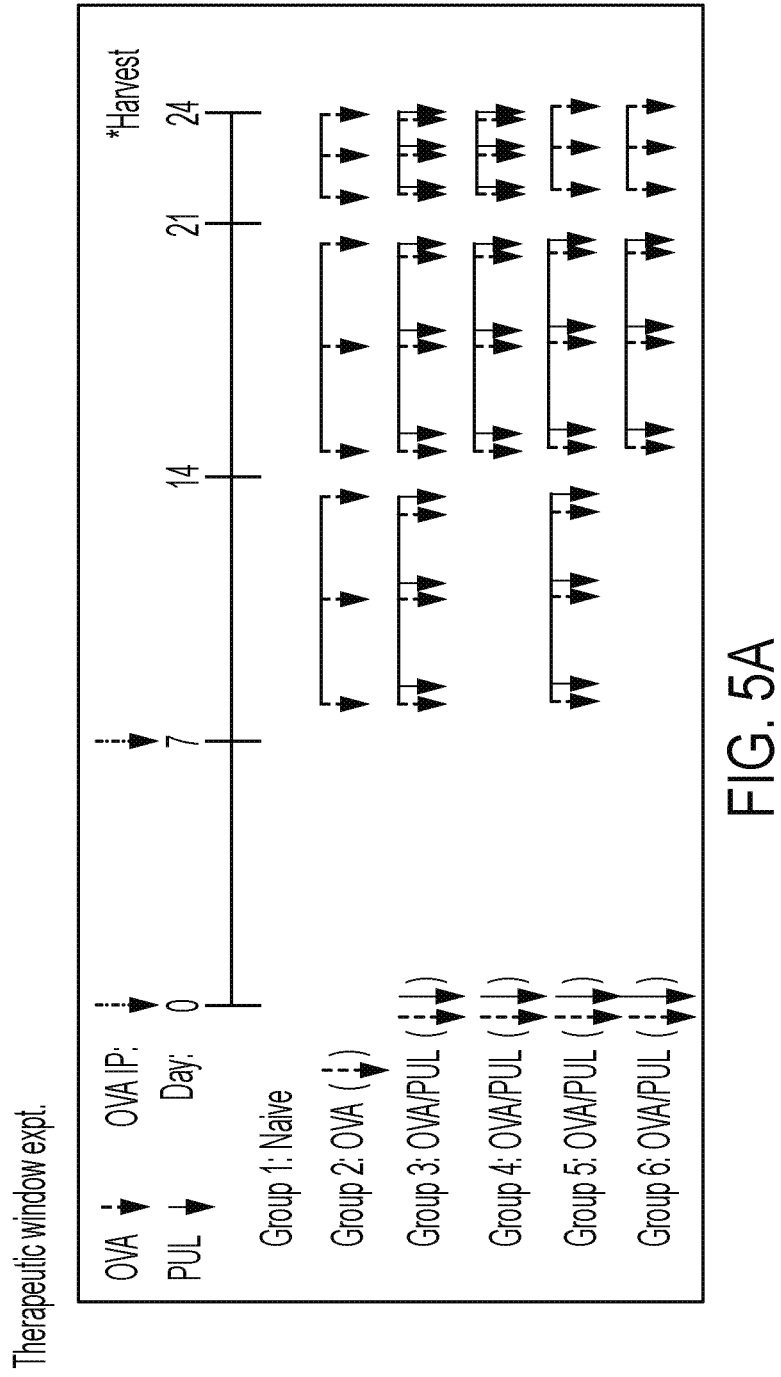

After establishing an optimal allergic sensitization/aerosol challenge model, the inventors sought to define the following parameters regarding aerosol administration of OVA-O/P: (1) minimum number of aerosol administrations; and (2) timing of aerosol treatments. To this end, a comprehensive experiment was designed where mice were immunized twice with OVA and aerosol challenged with either OVA alone (Group 2), or with OVA-O/P at various intervals as illustrated in FIG. 5A.

To evaluate the effects of aerosolized OVA-O/P on airway inflammation, total and specific cells counts were performed in the BAL of aerosol-challenged mice (FIG. 5B). Whereas all five groups of mice challenged with OVA had increased total cell counts (FIG. 5B), only mice in Group 3 showed a marked reduction in airway EOS, indicating a successful block in eosinphilic infiltration. In addition, mucin density analysis of lung tissue sections correspondingly revealed that mice in Group 3 had the lowest mucin density score as compared to all other groups (FIG. 5C).

Figure 6:
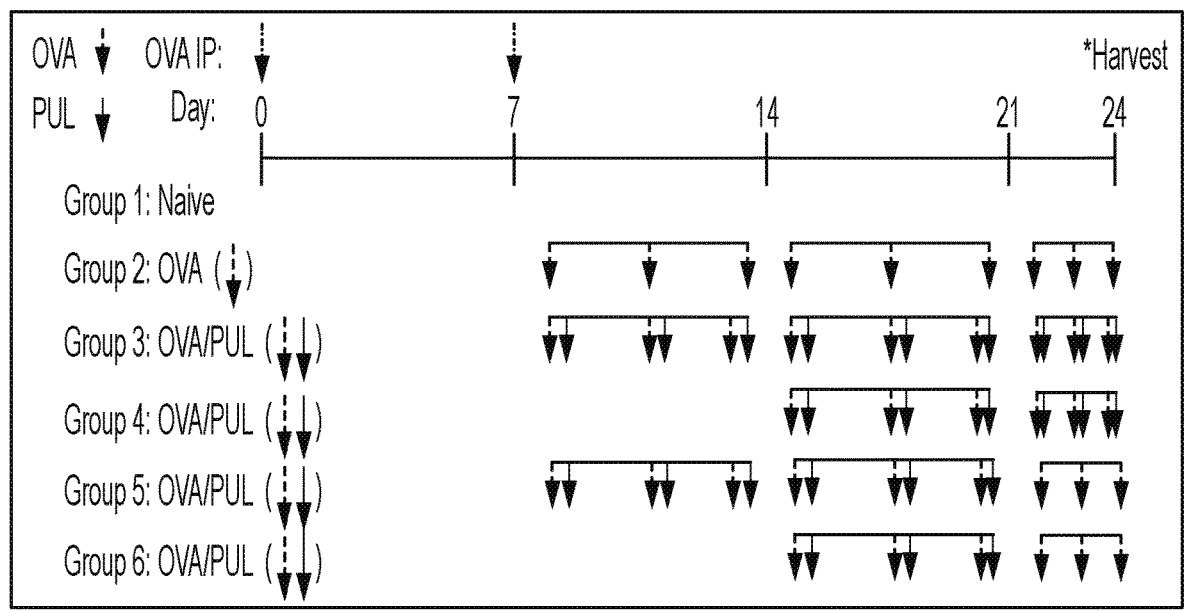
FIG. 6. Determination of most efficacious window with aerosolized OVA-0/P by immunoglobulin analysis. Balb/c mice (n=10) were immunized and aerosol challenged as described in FIG. 5A and illustrated in left panel. Sandwich ELISAs were used to measure total IgE, OVA IgE, OVA IgG1, and IgG2a levels from mouse serum samples (n=10). Comparison of total IgE in OVA treated mice (top panel, Group 2, 24.66±8.23) with OVA-O/P (Group 3 11.15±2.61) revealed a slight decrease in IgE levels. In addition, comparison of OVA-IgE in OVA treated mice (second panel, Group 2, 3.77±1.00) with OVA-O/P (Group 3, 2.14±0.34) revealed a decrease in OVA-IgE levels.
Figure 6:
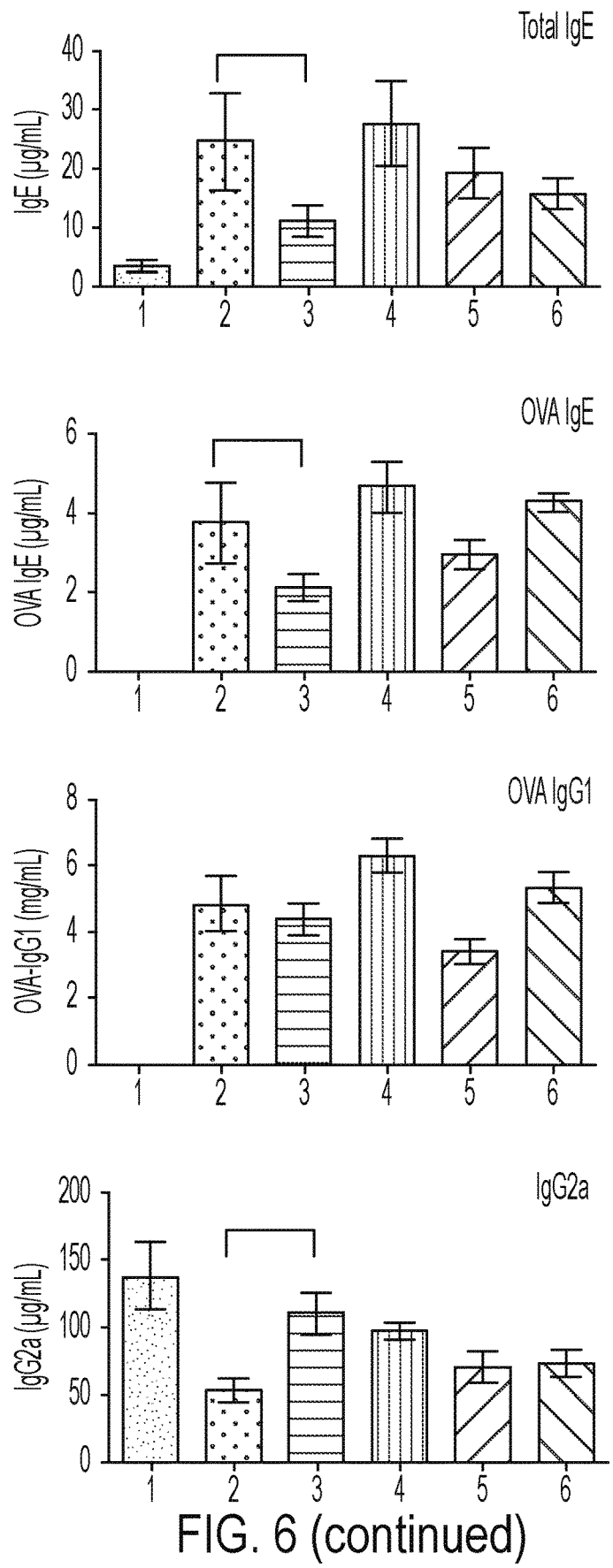

Comparison of total IgE in OVA treated mice (FIG. 6, top panel, Group 2, 24.66±8.23) with OVA-O/P (Group 3 11.15±2.61) correspondingly revealed a decrease in IgE levels. Analysis of OVA-IgE in OVA treated mice (FIG. 6, second panel, Group 2, 3.77±1.00) with OVA-O/P (Group 3, 2.14±0.34) revealed the same trend. Lastly, a reciprocal trend was observed in serum IgG2a levels in these two groups (Group 2 and 3), indicating an increased Th1 immune response in mice treated with aerosolized OVA-O/P.

In sum, these data indicate that aerosol treatments of O/P+OVA given over two and half weeks modulate allergic Th2 response to a less allergic phenotype and reduce airway inflammation.

B. Materials and Methods

Mice.

Female BALB/c mice (6-10 weeks of age) were purchased from Charles River, Wilmington, Mass., and housed five mice per cage in a 12/12 h light/dark cycle with food and water available ad libitum. All experimental procedures were approved by the institutional animal ethics committee (IAUCUC) at the Institute of Biosciences and Technology, Texas A&M HSC.

Sensitization and Airway Challenge with OVA-O/P.

Synthetic TLR ligands (referred to as O/P) were purchased from InvivoGen (San Diego, Calif.), reconstituted in endotoxin-free water, and suspended in 8 ml sterile PBS at the following concentrations: Pam2 10 µg/ml; ODN2395 20 µg/ml. Mice were sensitized to ovalbumin (OVA) (20 g OVA, Grade V, 2.25 mg alum in saline, pH7.4; Sigma, St. Louis, Mo.) administered by intraperitoneal (IP) injection once weekly for one or two weeks. Sensitized mice were exposed for 30 min to an aerosol of 2.5% (wt/vol) ovalbumin in 0.9% saline, via Aerotech II nebulizer (CIS US, Inc.) combined with or without O/P in the presence of room air supplemented with 5% $CO_2$ to promote maximal ventilation and homogeneous aerosol exposure throughout the lungs.

Enzyme-Linked Immunosorbent Assay for Immunoglobulin Measurement.

Serum immunoglobulin concentrations were determined by standard sandwich ELISA technique using 96 well Easywash high binding flat bottom plates (Corning). All reagents were diluted in assay diluent (TBS+0.1% BSA [Calbiochem]) except for the coating reagent, which was diluted in TBS only. All wells were washed with wash buffer (TBS+0.1% Tween-20) 3×s, 5 minutes per wash, and all samples developed by adding TMB Substrate Reagent (BD Biosciences) for 30 minutes in the dark. Reactions were stopped by addition of 2N $H_2SO_4$ and absorbance read at 450 nm. All readings used in the data fell within the linear portion of the standard curves.

For OVA IgE ELISAs, wells were coated with 2 μg/mL goat anti-mouse IgE (AbD Serotec, STAR166) overnight at 4° C. After washing, mouse anti-OVA IgE standards (AbD Serotec, clone 2C6) or diluted mouse serum samples (usually 1:50) were incubated for 1 h at 37° C. After washing, 10 μg/mL biotin-conjugated OVA (EZ-Link Sulfo-NHS-LC-Biotin, Thermo Scientific) were incubated for 1 h at 37° C. Wells were washed as indicated and 1:5,000 Neutravidin-HRP (Thermo Scientific) was incubated for 30 minutes at 37° C., followed by two more washes with TBS before developing the samples.

The same protocol was followed for determining total IgE using the following amounts of reagents: 2 μg/mL goat anti-mouse IgE (AbD Serotec, STAR166), 2 μg/mL Biotin Rat Anti-Mouse IgE (BD Biosciences, clone R35-118). For OVA IgG1, the following amounts of reagents were used: 100 μg/mL OVA (Sigma) and 0.1 μg/mL Biotin Rat Anti-Mouse IgG1 (eBioscience, clone M1-14D12). For total IgG1: 2 μg/mL Rat Anti-Mouse IgG1 (BioLegend, clone RMG1-1), 0.05 μg/mL Biotin Rat Anti-Mouse IgG1 (eBioscience, clone M1-14D12). For IgG2a: 2 μg/mL Rat Anti-Mouse IgG2a (BioLegend, clone RMG2a-62) and 0.05 μg/mL Biotin Goat Anti-Mouse IgG2a (AbD Serotec, 108008). For total IgG: 2 μg/mL Goat Anti-Mouse IgG (AbD Serotec, 103001) and 0.025 μg/mL Biotin Sheep Anti-Mouse IgG (AbD Serotec, AAC10B).

Bronchoalveoloar Lavage (BAL) Fluid Preparation and Cell Analysis.

BAL was obtained by instilling and withdrawing two, 1 ml aliquots of PBS via trachea cannula (luer stub adapter, BD Biosciences). Total leukocyte count was determined with a hemocytometer (Houser Scientific, Horsham, Pa.), and slides for differential cell count were prepared by cytospin of 300 μl of BAL fluid at 500×g for 5 min, followed by Wright-Giemsa staining.

Statistical Analysis.

Two groups of data were compared using the Student t test. The P value for significance was set at less than 0.05. All results were expressed as the mean±SEM, and all groups had 10 mice/experimental condition (n=10), unless stated otherwise.

The invention claimed is:

1. A method for attenuating type I hypersensitivity in a subject, comprising administering an effective amount of at a composition comprising PAM2CSK4 and ODNM362 to a subject susceptible to allergen induced asthma.

2. The method of claim 1, wherein the subject has been exposed to the allergen.

3. The method of claim 1, wherein the molar ratio of PAM2CSK to ODNM362 is 4:1.

4. The method of claim 1, wherein the subject has allergic asthma.

5. A method for attenuating type I hypersensitivity in a subject, comprising administering an effective amount of a composition comprising TLR agonists and an allergen to a subject susceptible to allergen induced asthma; wherein the TLR agonists consist of PAM2CSK4 and ODNM362.

6. A pharmaceutically acceptable composition comprising PAM2CSK4, ODNM362, and an asthma-inducing allergen.

7. The composition of claim 6, wherein the composition further comprises an anti-inflammatory agent.

8. The composition of claim 7, wherein the anti-inflammatory agent is budesonide.

9. The composition of claim 6, wherein the composition is sterile and essentially free of pathogenic microbes.

* * * * *

SEQUENCE LISTING

<160> NUMBER OF SEQ ID NOS: 5

<210> SEQ ID NO 1
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 1
tcgtcgtttt cggcgcgcgc cg                                            22

<210> SEQ ID NO 2
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 2
tcgtcgtcgt tcgaacgacg ttgat                                         25

<210> SEQ ID NO 3
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 3
tcgtcgtttt cgcgcgcgcc g                                             21

<210> SEQ ID NO 4
<211> LENGTH: 9
<212> TYPE: DNA
<213> ORGANISM: Artificial Sequence
<220> FEATURE:
<223> OTHER INFORMATION: Synthetic Oligonucleotide

<400> SEQUENCE: 4 cgcgaagcg                                                            9

```
<210> SEQ ID NO 5
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 5
agggttaggg ttagggttag gg                                              22
```

UNITED STATES PATENT AND TRADEMARK OFFICE
CERTIFICATE OF CORRECTION

| | |
|---|---|
| PATENT NO. | : 11,826,422 B2 |
| APPLICATION NO. | : 16/348829 |
| DATED | : November 28, 2023 |
| INVENTOR(S) | : Burton F. Dickey et al. |

It is certified that error appears in the above-identified patent and that said Letters Patent is hereby corrected as shown below:

On the Title Page

(63) Related U.S. Application Data:
Delete "Continuation of" and replace with -- Provisional --.

Signed and Sealed this
Thirteenth Day of February, 2024

Katherine Kelly Vidal
*Director of the United States Patent and Trademark Office*